United States Patent
Ngo et al.

(10) Patent No.: US 9,301,702 B2
(45) Date of Patent: Apr. 5, 2016

(54) SYSTEMS AND METHODS FOR EXPLOITING PULMONARY ARTERY PRESSURE OBTAINED FROM AN IMPLANTABLE SENSOR TO DETECT CARDIAC RHYTHM IRREGULARITIES

(71) Applicant: PACESETTER, INC., Sylmar, CA (US)

(72) Inventors: Thao Ngo, Shakopee, MN (US); Kathleen Kresge, Minneapolis, MN (US); Michael Kane, Pewaukee, WI (US); Scott Patrick Simon, Billings, MT (US)

(73) Assignee: PACESETTER, INC., Sylmar, CA (US)

( * ) Notice: Subject to any disclaimer, the term of this patent is extended or adjusted under 35 U.S.C. 154(b) by 671 days.

(21) Appl. No.: 13/681,241

(22) Filed: Nov. 19, 2012

(65) Prior Publication Data
US 2014/0142443 A1 May 22, 2014

(51) Int. Cl.
*A61B 5/02* (2006.01)
*A61B 5/024* (2006.01)
*A61B 5/00* (2006.01)
(Continued)

(52) U.S. Cl.
CPC ............ *A61B 5/02405* (2013.01); *A61B 5/0006* (2013.01); *A61B 5/02152* (2013.01); *A61B 5/4836* (2013.01); *A61B 5/686* (2013.01); *A61B 5/7246* (2013.01); *A61B 5/7278* (2013.01); *A61B 5/7282* (2013.01); *A61N 1/3627* (2013.01); *A61N 1/3684* (2013.01)

(58) Field of Classification Search
CPC .................................. A61B 5/02; A61B 5/021
See application file for complete search history.

(56) References Cited

U.S. PATENT DOCUMENTS

| | | | |
|---|---|---|---|
| 4,984,572 A | 1/1991 | Cohen | |
| 4,986,270 A | 1/1991 | Cohen | |

(Continued)

FOREIGN PATENT DOCUMENTS

| | | |
|---|---|---|
| WO | 2007002888 A1 | 1/2007 |
| WO | 2007078421 A2 | 7/2007 |

(Continued)

OTHER PUBLICATIONS

Abraham, William T. et al., "Wireless pulmonary artery haemodynamic monitoring in chronic heart failure: a randomised controlled trial," Lancet. 2011;377:658-666.

(Continued)

*Primary Examiner* — Etsub Berhanu

(57) ABSTRACT

Techniques are provided for use with a pulmonary artery pressure (PAP) monitor having an implantable PAP sensor. In one example, a PAP signal is sensed that is representative of beat-by-beat variations in PAP occurring during individual cardiac cycles of the patient. The PAP monitor detects intervals within the signal corresponding to the durations of cardiac cycles, then detects cardiac rhythm irregularities based on the intervals. For example, the PAP monitor can detect and distinguish atrial fibrillation, ventricular fibrillation and ventricular tachycardia based on the stability of the intervals of the PAP signal along with other information such as ventricular rate. The PAP monitor can also detect and distinguish premature contractions based on durations of the intervals. Examples where the PAP monitor is a component of an implantable cardiac rhythm management device (CRMD) are also provided.

25 Claims, 13 Drawing Sheets

(51) Int. Cl.
*A61B 5/0215* (2006.01)
*A61N 1/362* (2006.01)
*A61N 1/368* (2006.01)

(56) References Cited

U.S. PATENT DOCUMENTS

| | | | |
|---|---|---|---|
| 5,163,429 | A | 11/1992 | Cohen |
| 6,277,078 | B1 | 8/2001 | Porat et al. |
| 7,139,609 | B1 | 11/2006 | Min et al. |
| 7,147,604 | B1 | 12/2006 | Allen et al. |
| 7,248,925 | B2 | 7/2007 | Bruhns et al. |
| 7,272,436 | B2 | 9/2007 | Gill et al. |
| 7,590,446 | B1 | 9/2009 | Min et al. |
| 7,621,036 | B2 | 11/2009 | Cros et al. |
| 7,632,235 | B1 | 12/2009 | Karicherla et al. |
| 7,666,144 | B2 | 2/2010 | Cohen et al. |
| 7,706,865 | B1 | 4/2010 | Snell |
| 7,751,889 | B1 | 7/2010 | Schecter |
| 7,848,793 | B1 | 12/2010 | Shelchuk et al. |
| 7,909,770 | B2 | 3/2011 | Stern et al. |
| 7,949,394 | B2 | 5/2011 | Salo et al. |
| 7,957,802 | B2 | 6/2011 | Patangay et al. |
| 7,974,687 | B1 | 7/2011 | Farazi et al. |
| 8,021,307 | B2 | 9/2011 | White et al. |
| 8,118,749 | B2 | 2/2012 | White et al. |
| 8,126,552 | B2 | 2/2012 | Min et al. |
| 8,145,311 | B2 | 3/2012 | Min |
| 8,249,707 | B2 | 8/2012 | Nabutovsky et al. |
| 8,265,755 | B2 | 9/2012 | Min |
| 2002/0019593 | A1* | 2/2002 | Hsu et al. ............... 600/513 |
| 2002/0035335 | A1* | 3/2002 | Schauerte ............... 600/518 |
| 2002/0087091 | A1* | 7/2002 | Koyrakh et al. ........ 600/521 |
| 2002/0143265 | A1* | 10/2002 | Ackerman et al. ...... 600/515 |
| 2004/0167510 | A1* | 8/2004 | Feld et al. .............. 606/41 |
| 2004/0255959 | A1* | 12/2004 | Ducharme et al. ...... 128/898 |
| 2005/0288725 | A1* | 12/2005 | Hettrick et al. ......... 607/17 |
| 2006/0047205 | A1 | 3/2006 | Ludomirsky et al. |
| 2006/0200030 | A1 | 9/2006 | White et al. |
| 2006/0283007 | A1 | 12/2006 | Cros et al. |
| 2006/0287602 | A1 | 12/2006 | O'Brien et al. |
| 2006/0287700 | A1 | 12/2006 | White et al. |
| 2007/0197921 | A1 | 8/2007 | Cohen et al. |
| 2008/0288013 | A1 | 11/2008 | Schecter |
| 2009/0054945 | A1 | 2/2009 | Patangay et al. |
| 2009/0118783 | A1 | 5/2009 | Patangay et al. |
| 2009/0299423 | A1 | 12/2009 | Min |
| 2010/0094144 | A1 | 4/2010 | Doron |
| 2010/0099993 | A1 | 4/2010 | Cohen et al. |
| 2010/0114228 | A1 | 5/2010 | Bharmi et al. |
| 2011/0022112 | A1 | 1/2011 | Min |
| 2011/0066055 | A1 | 3/2011 | Bharmi et al. |
| 2011/0178565 | A1* | 7/2011 | Li et al. ................. 607/17 |
| 2012/0136406 | A1 | 5/2012 | Min |
| 2012/0158079 | A1 | 6/2012 | Rosenberg et al. |
| 2012/0165892 | A1 | 6/2012 | Min et al. |
| 2012/0209345 | A1* | 8/2012 | Shkurovich et al. ..... 607/23 |
| 2013/0204147 | A1* | 8/2013 | Blomqvist et al. ...... 600/486 |

FOREIGN PATENT DOCUMENTS

| | | |
|---|---|---|
| WO | 2007133873 A2 | 11/2007 |
| WO | 2007078421 A3 | 12/2007 |
| WO | 2007133873 A3 | 1/2008 |
| WO | 2009025667 A1 | 2/2009 |
| WO | 2009025734 A1 | 2/2009 |
| WO | 2010042291 A1 | 4/2010 |
| WO | 2010059291 A1 | 5/2010 |

OTHER PUBLICATIONS

Furberg, Curt D. MD, PhD et al., "Prevalence of Atrial Fibrillation in Elderly Subjects (the Cardiovascular Health Study)," Am J Cardiol. 1994;74:236-241.

Kannel, William B. MD et al., "Epidemiologic Features of Chronic Atrial Fibrillation," N Eng J Med. 1982;306:1018-1022.

Mark, Jonathan B. MD, Atlas of Cardiovascular Monitoring. New York, Churchill Livingstone. 1998: Fig 17.11.

St. Jude Medical Laptop-HF Newsletter. Issue No. 2, vol. 2, Jun. 15, 2012, 7 pages.

* cited by examiner

```
┌─────────────────────────────────────────────────────────┐
│  EXEMPLARY TECHNIQUE FOR EXPLOITING PAP SIGNAL          │
│  STABILITY TO DETECT CARDIAC RHYTHM IRREGULARITIES      │
└─────────────────────────────────────────────────────────┘
                           │
                           ▼
```

SENSE PAP SIGNAL USING A PAP SENSOR AND IDENTIFY PULMONARY ARTERY SYSTOLE (PAS) POINTS, PULMONARY ARTERY DIASTOLE (PAD) POINTS AND/OR DICROTIC NOTCHES AND MEASURE INTERVALS BETWEEN CONSECUTIVE POINTS CORRESPONDING TO THE DURATIONS OF INDIVIDUAL CARDIAC CYCLES — 300

FOR A GIVEN INTERVAL (SUCH AS THE PAD-PAD INTERVAL), ASSESS INTERVAL STABILITY BY: IDENTIFYING AND REJECTING THE LONGEST AND SHORTEST INTERVALS, IDENTIFYING AND SELECTING THE SECOND LONGEST AND SECOND SHORTEST INTERVALS, THEN DETERMINING THE DIFFERENCE BETWEEN THE SECOND LONGEST AND SECOND SHORTEST INTERVALS FOR USE A STABILITY INDICATOR/SCORE (OR CALCULATE AVERAGE PAP WAVEFORM INTERVAL STABILITY VALUE AND COMPARE TO A BASELINE PAP WAVEFORM INTERVAL STABILITY TO GENERATE THE STABILITY INDICATOR/SCORE) — 310

COMPARE STABILITY INDICATOR/SCORE TO A STABILITY THRESHOLD SET BASED ON A PREPROGRAMMED VALUE OR A PREDETERMINED PATIENT STABILITY BASELINE SUCH AS A THRESHOLD OF 40MS — 332

FIG. 4A

334 — PAP SIGNAL STABLE? 
 — STABLE → DISTINGUISH BETWEEN VT AND NORMAL SINUS RHYTHM (FIG. 8) — 370
 — INSTABLE ↓

DETERMINE VENTRICULAR RATE BASED ON DURATION OF THE INTERVALS AND COMPARE AGAINST A PRESET TACHYCARDIA RATE THRESHOLD — 336

TO FIG. 4B

SYSTEMS AND METHODS FOR EXPLOITING PULMONARY ARTERY PRESSURE OBTAINED FROM AN IMPLANTABLE SENSOR TO DETECT CARDIAC RHYTHM IRREGULARITIES

CROSS REFERENCE TO RELATED APPLICATIONS

This application is related to U.S. patent application Ser. No. 13/681,273, filed concurrently herewith, titled "Systems and Methods for using Pulmonary Artery Pressure from an Implantable Sensor to Detect Mitral Regurgitation and Optimize Pacing Delays".

FIELD OF THE INVENTION

The invention generally relates to implantable medical devices and external systems for use therewith and, in particular, to techniques for detecting and discriminating cardiac rhythm irregularities using pulmonary artery pressure, particularly within heart failure patients.

BACKGROUND OF THE INVENTION

Heart failure (HF) is a debilitating disease in which abnormal function of the heart leads in the direction of inadequate blood flow to fulfill the needs of the tissues and organs of the body. Typically, the heart loses propulsive power because the cardiac muscle loses capacity to stretch and contract. Often, the ventricles do not adequately eject or fill with blood between heartbeats and the valves regulating blood flow become leaky, allowing regurgitation or back-flow of blood. The impairment of arterial circulation deprives vital organs of oxygen and nutrients. Fatigue, weakness and the inability to carry out daily tasks may result. Not all HF patients suffer debilitating symptoms immediately. Some may live actively for years. Yet, with few exceptions, the disease is relentlessly progressive. As HF progresses, it tends to become increasingly difficult to manage. Even the compensatory responses it triggers in the body may themselves eventually complicate the clinical prognosis. For example, when the heart attempts to compensate for reduced cardiac output, it can add muscle causing the ventricles (particularly the left ventricle) to grow in volume in an attempt to pump more blood with each heartbeat. This places a still higher demand on the heart's oxygen supply. If the oxygen supply falls short of the growing demand, as it often does, further injury to the heart may result. The additional muscle mass may also stiffen the heart walls to hamper rather than assist in providing cardiac output, resulting in elevated pressures within the left atrium. Elevated left atrial pressure (LAP) can then exacerbate the HF, particularly congestive HF where the weak pumping of the heart leads to a build-up of fluids in the lungs and other organs and tissues. Often, a progression of HF and the build-up of congestive fluids results in the patient being hospitalized.

Despite current therapies, the rate of HF hospitalizations remain high—about 1.1 million HF hospitalizations annually. A new approach to managing patients has exploited chronic measurements of pulmonary arterial pressures. Pulmonary artery pressure (PAP) is generated by the right ventricle (RV) ejecting blood into the pulmonary circulation, which acts as a resistance to the output from the RV. With each ejection of blood during ventricular systole, pulmonary arterial blood volume increases which stretches the wall of the artery. As the heart relaxes, blood continues to flow from the pulmonary artery into the pulmonary circulation. The smaller arteries and arterioles serve as the chief resistance vessels, and through changes in their diameter, regulate pulmonary vascular resistance. In the recent CHAMPION study, the use of a wireless implantable PAP sensor showed a 30% percent reduction in HF hospitalizations in six months in New York Heart Association (NYHA) Class III HF patients in a prospective, multi-center, randomized (1:1) controlled single blinded clinical trial (n=553). (See, Abraham et al., "Wireless pulmonary artery haemodynamic monitoring in chronic heart failure: a randomised controlled trial," Lancet 2011; 377:658-666.) Use of daily PAP measurements allowed physicians to proactively monitor and tailor the patient's pharmacological therapy. Note that the CHAMPION study was directed to the use of a PAP sensor provided by CardioMEMS, Inc., which operates in conjunction with an external PAP monitor. Briefly, the PAP sensor is implanted within the pulmonary artery of the patient using a catheter. Thereafter, once per day (or at some other periodic interval), the patient places an interface device over his or her chest, which receives PAP data wirelessly from the implanted sensor for routing to a clinician for review.

Although PAP monitors of the type used in the CHAMPION study are quite useful, such systems currently provide no atrial pulsatile hemodynamic data, which would be helpful to the clinician. Moreover, in circumstances where atrial fibrillation (AF) induces an increase in LAP within the patient (thereby also increasing end diastolic PAP), there appears to be no current method to distinguish this condition from increases in LAP associated with HF progression. Accordingly, it would be desirable to provide PAP-based techniques for distinguishing changes in PAP due to AF or other arrhythmias from changes due to progression of HF. This would allow the clinician to more effectively establish an appropriate treatment plan (e.g. to determine whether pharmacological adjustments are warranted or AF ablations should be performed.)

In this regard, note that AF is the most common arrhythmia. According to the Framingham Heart Study, AF has a prevalence of about 4% in the adult population. (See, Kannel et al, "Epidemiologic features of chronic atrial fibrillation: The Framingham Study," NEJM. 1982; 306:1018-22.) As the patient population continues to age, the prevalence of AF rises as well, from less than 0.05 percent in patients 25 to 35 years of age to more than 5% patients over 69 years of age. (See, Furberg et al., "Prevalence of atrial fibrillation in elderly subjects (The Cardiovascular Health Study)," Am J Cardiol. 1994; 74:236-241.) In the HF patient population, AF, premature ventricular contractions (PVCs) and ventricular arrhythmias are a common co-morbidity. In the Framingham Heart Study, 1470 participants developed either HF or a new AF between the years 1948 and 1995. Moreover, the prevalence of AF in patients with HF increased in parallel with the severity of the disease, ranging from 5% in patients with mild HF to 10% to 26% among patients with moderate HF and up to 50% in patients with severe HF.

SUMMARY OF THE INVENTION

In a first embodiment, systems and methods are provided for use with a medical system having an implantable PAP sensor for implant within a patient. A time-varying PAP signal is sensed that is representative of variations in PAP occurring during individual cardiac cycles of the patient (i.e. the signal includes pulsatile variations due to the beating of the chambers of the heart.) The system detects intervals within the signal corresponding to durations of the cardiac cycles, then detects cardiac rhythm irregularities based on the intervals within the PAP signal. For example, the system can detect and distinguish AF, ventricular fibrillation (VF) and ventricular tachycardia (VT) based on the stability of the intervals in combination with other factors such as the ventricular rate. The system can also detect and distinguish PVCs and premature atrial contractions (PACs) based on the durations of the intervals.

In one embodiment, the system comprises an external PAP monitor for use with an implantable PAP sensor, wherein the analysis of the PAP signal is performed by the external monitor (or by other external systems) based on PAP signals received from the implanted sensor (wirelessly or otherwise.) Additionally or alternatively, the PAP-based discrimination methods may be exploited by CRMDs equipped with PAP sensors. For external PAP monitors, the detection and discrimination methods described herein allow the monitor to detect arrhythmias and other irregular cardiac rhythms without the need to also sense electrical cardiac signals such as surface electrocardiograms (EKGs). Hence, a relatively simple and inexpensive PAP monitor can be equipped to detect arrhythmias and other irregular cardiac rhythms, while also collecting and recording pulsatile PAP data to assist the clinician in managing the patient. In particular, the information obtained from the PAP regarding irregular cardiac rhythms can assist the clinician in distinguishing changes in PAP due to arrhythmia from changes due to progression of heart disease or other conditions. If high rate arrhythmias are found, this may indicate that the patient is a candidate for a CRMD (assuming one is not already implanted.) For CRMD-based implementations, the PAP-based methods described herein can be used to corroborate the detection of arrhythmias made based on intracardiac electrograms (IEGMs), while also providing useful PAP diagnostic information such as a PAP stability score for subsequent clinician review to aid in the management of HF or other conditions.

In an illustrative embodiment where the system includes an external PAP monitor for receiving PAP signals wirelessly from an implanted sensor, the system analyzes the PAP signals to detect fiducial points such as pulmonary artery systole (PAS) points, pulmonary artery diastole (PAD) points or dicrotic notches, then determines intervals between the points corresponding to the durations of cardiac cycles, such as the intervals between consecutive PAS peaks. The system then assesses the stability of the intervals to detect cardiac rhythm irregularities. In one specific example, the system tracks PAS-PAS intervals over a plurality of cardiac cycles, identifies and rejects the longest and shortest intervals, then identifies and selects the second longest and second shortest intervals. The difference between the second longest and second shortest intervals is calculated for use as a stability indicator or score. In another specific example, the system instead calculates an average PAP waveform interval stability value, then compares it to a baseline PAP waveform to generate the stability indicator/score. Once the stability of the PAP signal has been quantified, the system compares the stability indicator to predetermined stability criteria and generates an indication of an irregular cardiac rhythm if the PAP signal is found to be unstable relative to the stability criteria. The stability criteria may be, for example, a programmed threshold value or patient baseline value. In this regard, regularly conducted (sinus/paced) beats with regular conduction will typically generate a high PAP stability indicator/score indicating a similarity to "normal rhythm." AF and frequent PVCs with irregular conduction will instead typically generate a low stability indicator/score.

In the case where an irregular cardiac rhythm is indicated based on a poor PAP interval stability score, the system then discriminates among different irregular cardiac rhythms based on the ventricular rate (which may be calculated from the duration of the intervals in the PAP signal corresponding to durations of cardiac cycles.) In one example, the system compares the ventricular rate against a predetermined tachycardia rate threshold and then generates an indication of AF with controlled ventricular response if the PAP intervals are unstable and the ventricular rate is below the tachycardia rate threshold. Otherwise, if the ventricular rate is high (while the PAP intervals are unstable), the system uses PAP waveform morphology and other parameters to distinguish VF from AF with rapid ventricular response. In this regard, the system detects the waveform morphology of the PAP signal and compares it to a baseline morphology value associated with normal sinus rhythm to generate a morphology match indicator. The system also detects PAS peaks within the PAP signal and assesses any significant reduction in PAS amplitude from a baseline average associated with a loss of cardiac output. If the PAS peaks are found to be relatively consistent and the morphology match indicator shows a relatively good morphological match, the irregular cardiac rhythm is deemed to be AF with rapid ventricular response. If the PAS peaks are instead found to be reduced and the morphology match indicator shows a poor morphology match, VF is thereby indicated and alarms are generated to alert caregivers or emergency personnel. For the case where the PAP intervals were initially found to be stable, the system distinguishes normal sinus rhythm from a possible VT based on the ventricular rate. That is, if the ventricular rate is above the tachycardia threshold (while the PAP intervals remain stable), VT is indicated. Otherwise, a normal sinus rhythm is indicated. Depending upon the implementation, the analysis of the PAP signal data may be performed in real-time while PAP data is collected within the patient (which is especially critical for the prompt detection of VF) or may be performed based on data previously detected and recorded.

As noted, the time-varying PAP signal can also be used to detect and distinguish PACs and PVCs. In one example, the system determines the duration of each new interval within the PAP signal that corresponds to a cardiac cycle and compares the duration against a premature contraction threshold. If the duration is below the threshold (i.e. the interval is too short), a premature contraction is thereby indicated. The system then distinguishes between PACs and PVCs based on waveform morphology and PAS peak deviation. As with the morphology/PAS check summarized above, the system assesses waveform morphology of the PAP signal to generate a morphology match indicator and also detects PAS peak amplitudes and assesses any significant reduction in PAS peak amplitude. Then, if the PAS peaks are relatively consistent and the morphology match indicator shows a relatively good morphology match, the system generates an indication of a PAC. If the PAS peaks are reduced and the morphology match indicator shows a poor morphology match, the system generates an indication of a PVC. The morphology matching may exploit kendall tau methods where a high kendall tau score indicates a match to an intrinsic conduction beat (hence marked as a PAC), whereas a low score denotes a PVC. In some examples, the system also exploits LAP signal data, which may be obtained from an LAP sensor (if provided) or may be derived from the PAP signal. In this regard, it has been found that PAP signals obtained from the aforementioned PAP sensors are strongly correlated to LAP, with the main difference being the gradient across the lungs and pulmonary veins. Accordingly, the methods summarized above are modified where appropriate to exploit atrial and ventricular components of an LAP waveform. However, rather than using interval stability for AF detection, the system exploits morphology matching as an indicator. In addition, if so equipped, the system can transform LAP signal data into the frequency spectrum to distinguish independent rhythms in at the atrium and ventricle or can evaluate the dominate frequency of the signal to segregate potential high-rate arrhythmias (based on an overall higher frequency). The system may also leverage IEGMs sensed at the sensor lead to differentiate atrial and ventricular mechanical LAP components when paired with atrial activation, or the device may examine dLAP/dt|min to differentiate atrial and ventricular components. In this regard, the atrial component should be slower than the ventricular component when compared to ventricular relaxation because of muscle mass. The separation of separate atrial and ventricular components also allows the system to detect and discriminate PACs/PVCs. Separation of the atrial and ventricular components may be performed by the system by windowing of the signal with one third of the interval being systolic (ventricular) and two thirds being the diastolic (atrial) window and then examining the peak amplitudes in those windows. Other chronic ventricular-based hemodynamic signals besides LAP and PAP may be exploited as well, assuming the system is equipped to obtain such signals.

When a cardiac rhythm irregularity is detected using any of these techniques, the system preferably records diagnostic information for clinician review such as the current PAP signal waveform, the location and size of fiducial points within the waveforms, the current ventricular rate, etc., and detects and records any trends in those parameters. In this manner, an external PAP monitor can provide significant diagnostic information to the clinician regarding cardiac health. In particular, the additional diagnostic information can aid the clinician in establishing a treatment plan for the patient such as to decide between an AF ablation, alternative pharmacological therapies or the need for anticoagulation medications, etc. For examples where the PAP-based techniques are exploited by a CRMD, the techniques summarized above can be performed based on pressure signals while the CRMD concurrently operates to detect and distinguish irregular cardiac rhythms based on IEGMs. The pressure-based signal analysis can be used to confirm detections made using IEGMs and can provide additional diagnostic data pertinent to PAP for subsequent clinician review to aid in patient diagnosis and treatment.

Hence, aspects of the invention are broadly directed to providing techniques for use within a wide variety of waveform devices (with or without an EGM). There is a large population of patients that will not receive a CRM device but may receive a PAP or similar device. For CRMDs, the capability to also analyze output (amplitude) would be complementary to the use of an EGM, while the other techniques serve to corroborate discriminations. In this regard, standard ICD, CRMDs and ICDs typically exploit their own arrhythmia detection procedures and so aspects of the invention are directed to supplementing such procedures so as to provide an additional mode of discriminating arrhythmias (such as between a supraventricular tachycardia (SVT) and a VT For example, if PAP systolic or a PAP area under the curve (i.e. pseudo cardiac output (CO) would be diminished substantially in VT/VF and may only drop 30% in instances of SVT (due to loss of atrial kick.) System and method implementations of these and other techniques are presented herein.

BRIEF DESCRIPTION OF THE DRAWINGS

Features and advantages of the described implementations can be more readily understood by reference to the following description taken in conjunction with the accompanying drawings.

FIGS. 4A and 4B illustrate an exemplary technique for use with the general method of FIG. 3, wherein the stability of PAP intervals is exploited to detect and discriminate arrhythmias such as AF;

DETAILED DESCRIPTION OF THE PREFERRED EMBODIMENTS

The following description includes the best mode presently contemplated for practicing the invention. This description is not to be taken in a limiting sense but is made merely to describe general principles of the invention. The scope of the invention should be ascertained with reference to the issued claims. In the description of the invention that follows, like numerals or reference designators will be used to refer to like parts or elements throughout.

Overview of PAP Monitoring Systems

Figure 1:
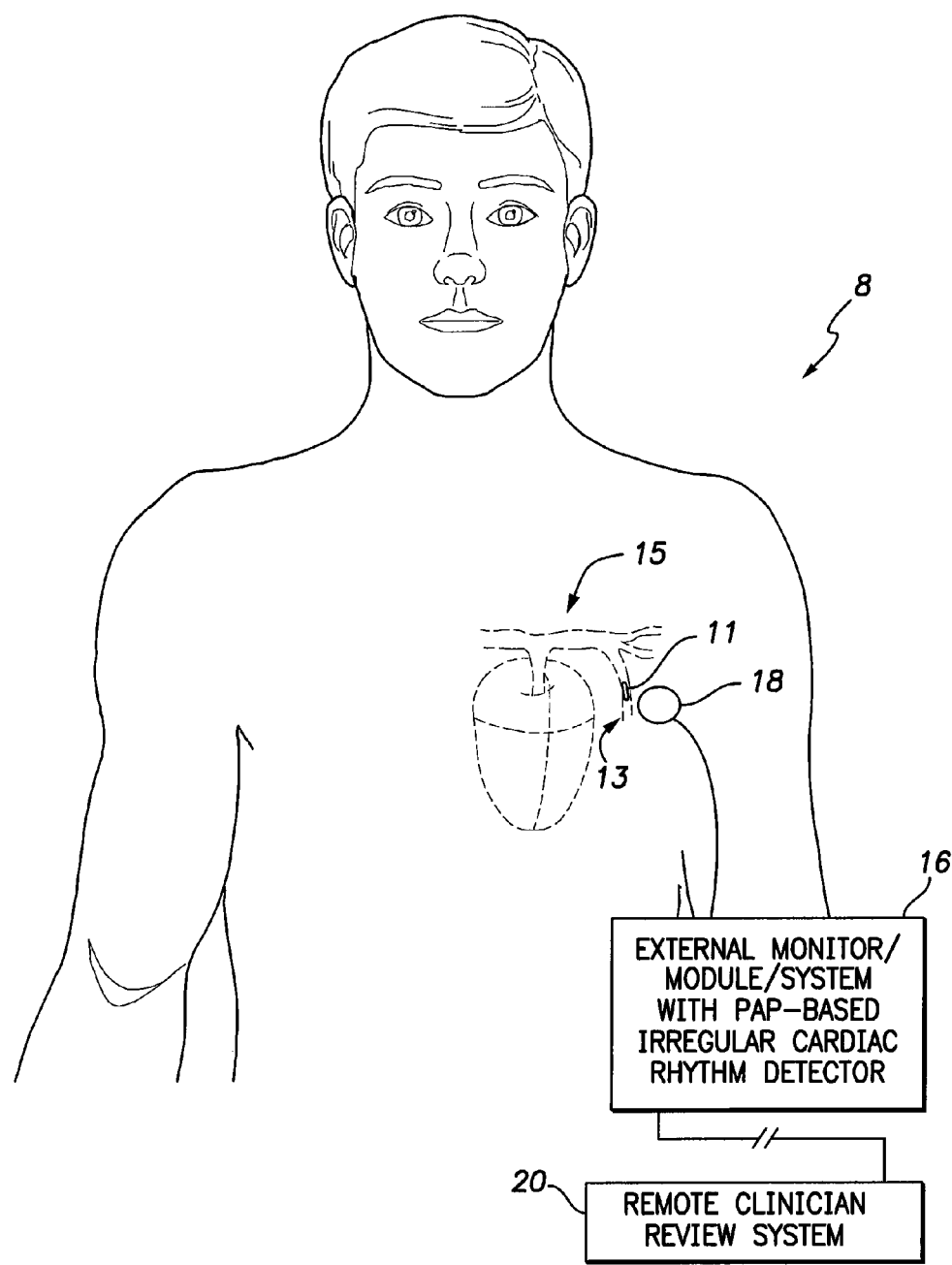
FIG. 1 illustrates a first exemplary PAP monitoring system having an external monitor equipped to detect and distinguish irregular cardiac rhythms based on PAP signals received from an implantable sensor.

FIG. 1 illustrates a first exemplary PAP monitoring system 8 equipped with a PAP sensor 11 implanted within one of the branches 13 of the pulmonary artery 15 for use with an external monitor, module or system 16. The external system receives signals from the PAP sensor for analysis to detect irregular cardiac rhythms and related conditions and to provide PAP-based diagnostic data such as a PAP stability score. To power the sensor and to retrieve data therefrom, the patient or caregiver places a wand 18 over the chest to deliver power to the implanted sensor via electromagnetic induction and receives wireless signals from a pressure transducer within the sensor for analysis. Then, external system 16 analyzes the PAP signals to detect irregular cardiac rhythms and related conditions and forwards the results to a remote clinician review system 20 for display. Note that external system 16 can comprise multiple components. For example, the system may include a bedside module for receiving PAP signals from wand 18 and a centralized processing system at a remote location that receives the PAP signals from the bedside module for analysis. The centralized system then forwards the results of its analysis (including the identification of any cardiac rhythm irregularities) to the clinician review system. In other implementations, the clinician review system instead performs the analysis based on PAP data it receives from system 16. In at least some embodiments, centralized computing systems such as the HouseCall™ system or the Merlin@home—Merlin.Net systems of St. Jude Medical may be used to relay or process at least some of the data.

Exemplary PAP sensors for use as sensor 11 are discussed in U.S. Pat. Nos. 7,621,036; 7,147,604; 8,021,307; 8,118,749; and 7,909,770, each initially assigned to CardioMems, Inc. See, also, the following U.S. Published Application Nos.: 2006/0200030; 2006/0283007; 2006/0287602; and 2006/0287700, of CardioMems. Note that FIG. 1 provides a stylized representation of the PAP sensor, the heart and the pulmonary artery vasculature to illustrate pertinent features of this exemplary embodiment of the invention. The actual shape and location of the PAP sensor may differ. Also, the figure is not intended to be anatomically accurate and, in particular, does not show the tissues connecting the base of the pulmonary artery to the RV via the mitral valve. A more accurate illustration of the heart and portions of the pulmonary artery is provided within FIG. 11, discussed below. Note also that wireless systems are not necessarily used. The system can instead exploit a lead-like sensor with a device (CRM or non-CRM) generating the power and performing the analysis.

Figure 2:
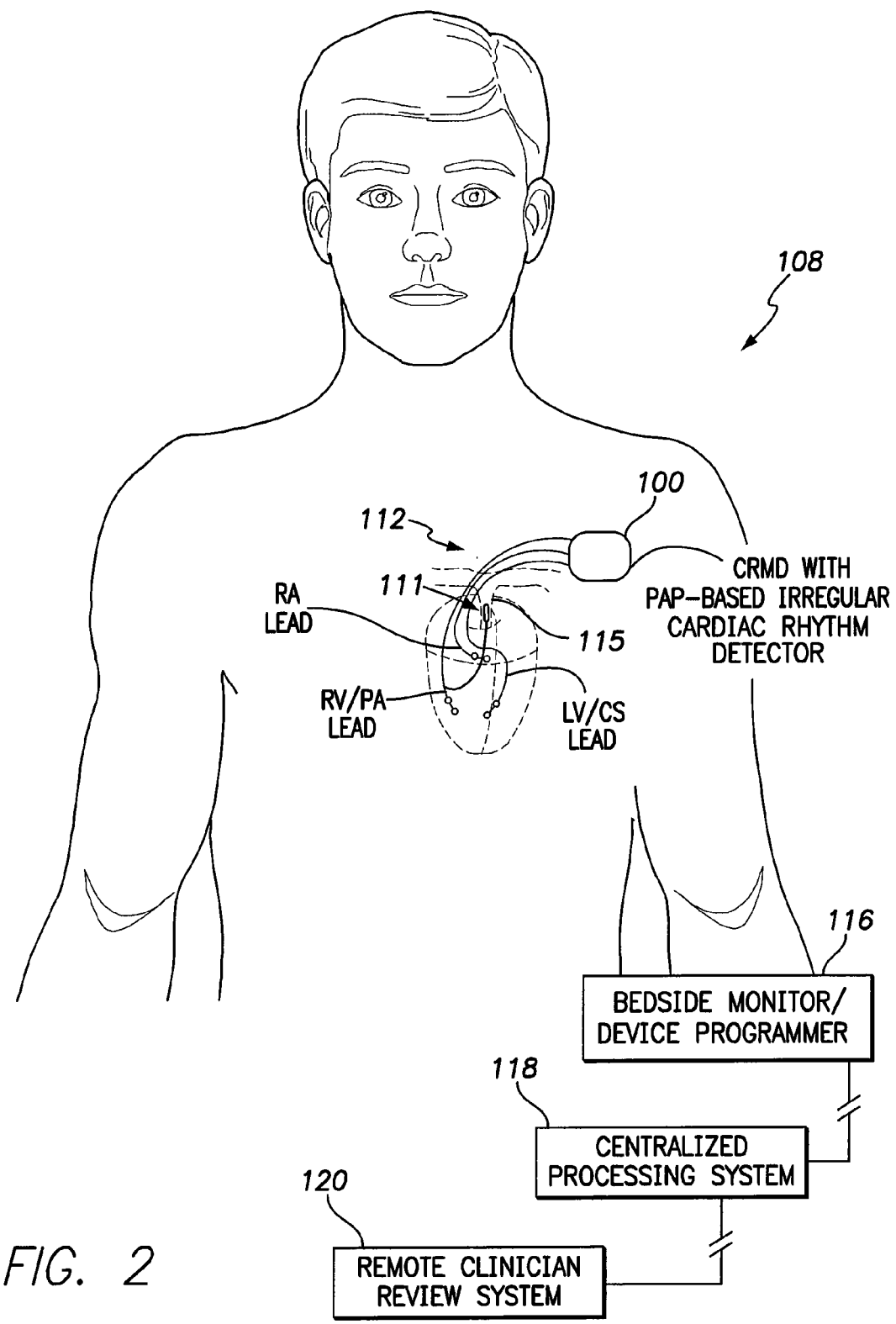
FIG. 2 illustrates a second exemplary PAP monitoring system wherein a CRMD is equipped to detect and distinguish irregular cardiac rhythms based on PAP signals received from an implantable sensor.

FIG. 2 illustrates a second exemplary system 108, which is equipped with a PAP sensor 111 implanted within the pulmonary artery 115 for use with a CRMD 100. The CRMD may be, for example, a pacemaker, CRT device, implantable cardioverter defibrillator (ICD) or other any suitably-equipped implantable medical device. In addition to performing cardiac rhythm management functions, CRMD 100 receives signals from the PAP sensor for analysis to confirm the detection of irregular cardiac rhythms and related conditions and to provide PAP-based diagnostic data. In this particular example, the PAP sensor is installed via an RV/PA lead, which includes a lead extension for positioning the sensor in the pulmonary artery. An example of this type of lead is described in U.S. Pat. No. 7,632,235 to Karicherla et al. Additional leads 112 are implanted on or within the heart of the patient, including an LV lead implanted via the coronary sinus (CS). In the example shown, the LV lead is a bipolar lead with a pair of tip/ring electrodes. In other examples, the LV lead may be a multi-pole lead (such as the Quartet™ lead provided by St Jude Medical, which is a quad-pole lead.) An exemplary RA lead is also shown. Both the RA and RV leads also include tip/ring electrode pairs. The various leads may also include coil electrodes as well as additional physiological sensors besides the PAP sensor. See FIG. 11, described below, for a more complete illustration of an exemplary lead system.

Depending upon the particular irregular cardiac rhythm that is detected, the device may issue warning signals. The warning signals may be generated to alert the patient using an internal warning device (which is part of the CRMD) or may be forwarded to an external device 116 such as a bedside monitor. The internal warning device may be a vibrating device, audible device or a "tickle" voltage device that, in either case, provides perceptible stimulation to the patient to alert the patient to consult a clinician or other caregiver. In one example, once the warning is felt, the patient positions an external device above his or her chest. The handheld device, which might be a personal advisory module (PAM), receives short-range telemetry signals from the implanted device and provides audible or visual verification of the warning signal. The handheld warning device thereby provides confirmation of the warning to the patient, who might otherwise be uncertain as to the reason for the internally generated warning signal. For further information regarding this type of warning/notification technique, see U.S. Pat. No. 7,272,436 to Gill et al.

If a bedside monitor or other external monitor is provided, the bedside monitor provides audible or visual alarm signals to alert the patient or caregivers, as well as providing textual or graphic displays. In addition, PAP data and other diagnostic information pertaining to irregular cardiac rhythms is transferred to the bedside monitor or is stored within the CRMD device for subsequent transmission to an external programmer for review by a clinician or other medical professional. The clinician may then prescribe therapies to address the condition. The clinician may also adjust the operation of the CRMD to activate, deactivate or otherwise control any therapies that are automatically applied. The bedside monitor may be networked with a centralized processing system 118 and/or a remote clinician review system 120 to immediately notify the clinician of any urgent medical condition. If VF or other life-threatening conditions are detected, emergency personnel are preferably notified immediately. Techniques for automatically notifying emergency personnel of serious medical conditions are discussed, for example, in U.S. Published Application 2011/0066055 of Bharmi et al.

Hence, FIGS. 1 and 2 provide an overview of exemplary medical systems for detecting and distinguishing irregular cardiac rhythms based on PAP, recording diagnostics, and delivering appropriate warning/notification signals, etc. Note that the particular locations of the implanted components shown in FIGS. 1 and 2 are merely illustrative and may not necessarily correspond to actual implant locations.

PAP-Based Techniques for Detecting Irregular Cardiac Rhythms

Figure 3:
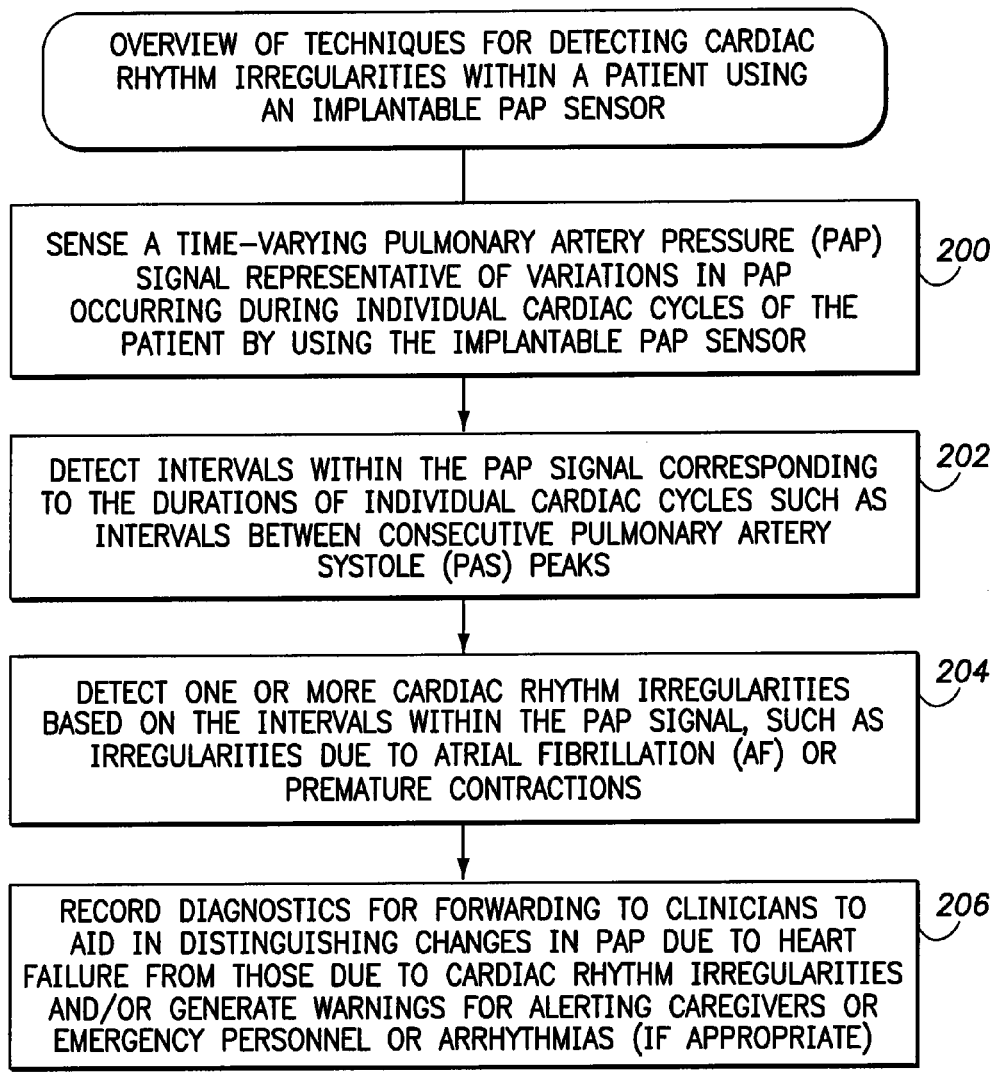
FIG. 3 summarizes a general technique that may be performed by the PAP monitoring systems of FIG. 1 or 2 to detect and distinguish irregular cardiac rhythms based on PAP signals.

FIG. 3 broadly summarizes the techniques exploited by the PAP monitoring systems of FIGS. 1 and 2 (or other suitably-equipped systems) for detecting and discriminating irregular cardiac rhythms. Briefly, at step 200, the system senses PAP signals using an implanted PAP sensor in communication with a PAP monitor (which, as noted, may be an external system or a component of a CRMD.) The sensed PAP waveform is primarily representative of pressure changes in the pulmonary artery and is typically composed of pulmonary artery systole (PAS), pulmonary artery diastole (PAD)/pulmonary artery end diastolic pressure (PAEDP), and dicrotic notch portions. At step 202, the system detects intervals within the PAP signal corresponding to the durations of individual cardiac cycles, such as intervals between consecutive PAS peaks. At step 204, the system detects one or more cardiac rhythm irregularities based on the intervals within the PAP signal, such as irregularities due to AF or PACs and PVCs. As will be described below, depending on the particular irregularities to be detected, this may involve analysis of PAP interval stability or PAP durations, or both, in combination with waveform morphology or other parameters. At step 206, the system records diagnostics for forwarding to the clinician to aid in distinguishing changes in PAP due to HF from those due to cardiac rhythm irregularities.

If PAP monitoring is performed once per day by an external system, the system can thereby provide daily trending of developing arrhythmias (including high ventricular rates, PACs, PVCs) while pairing that information with hemodynamic data such as PAP morphology data, PAS peak amplitudes, PAD peak amplitudes, etc. The technique can also improve PAP signal specificity by detecting outliers so as to allow removal of PVCs (and the compensatory beats following PVCs) from the PAP data while providing rate average and annotation of a PAP dataset (particularly when the patient is found to be in AF.) At step 206, the system can also generate warnings for immediately alerting caregivers or emergency personnel of arrhythmias (particularly if the PAP monitor is an on-board component of a CRMD and hence can analyze signals continuously and in real-time.) If a life threatening condition such as VF is detected, immediate notification of emergency personnel is critical.

The techniques described herein may be used in combination with systems and methods described in U.S. patent application Ser. No. 13/681,273 of Ngo et al., filed 11/19/2012, entitled "Systems and Methods for using Pulmonary Artery Pressure from an Implantable Sensor to Detect Mitral Regurgitation and Optimize Pacing Delays," which is fully incorporated by reference herein.

Turning now to FIGS. 4A-8, exemplary techniques for exploiting PAP interval stability to detect cardiac rhythm irregularities will be described in detail. At step 300, the PAP monitor senses the PAP signal using a PAP sensor and identifies PAS points, PAD points, dicrotic notches or other fiducial points and measures intervals between consecutive points corresponding to the durations of individual cardiac cycles. For example, the intervals between consecutive PAS peaks can be detected, measured and tracked. In one example, an eighteen second continuous PAP waveform is obtained in which intervals are detected, though shorter or longer segments of data may alternatively be collected for analysis. For implementations where an external PAP monitor is used, the data is collected periodically, such as once per day, or is collected on demand if the patient feels symptomatic.

Figure 5:
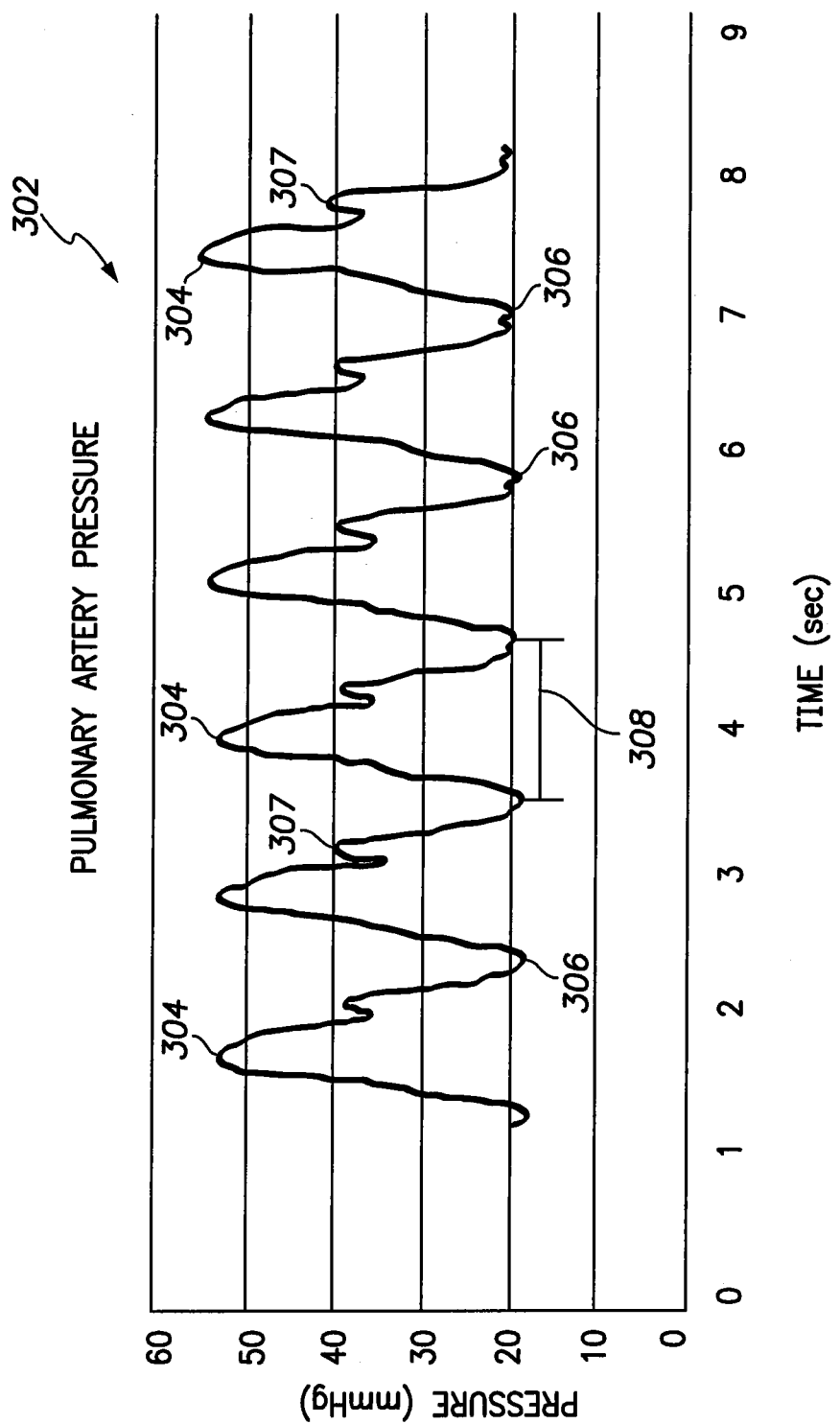
FIG. 5 graphically illustrates an exemplary PAP waveform that may be analyzed by the technique of FIGS. 4A and 4B, specifically highlighting fiducial points within the waveform that may be detected and exploited.

FIG. 5 illustrates a time-varying PAP signal or waveform 302 showing PAS points 304, as well as PAD/PAEDP points 306 and dicrotic notches 307. An exemplary interval 308 is shown between a pair of the PAD points, which corresponds to the duration of a corresponding cardiac cycle. Note, however, that the start and end points of the PAP interval will not necessarily correspond to the start and end points of the corresponding electrical cardiac cycle as observed within an IEGM or surface EKG. For example, within the IEGM an intrinsic cardiac cycle is typically deemed to begin with the P-wave (corresponding to atrial depolarization.) This is followed by an R-wave, which corresponds to ventricular depolarization. The R-wave is then followed by a T-wave (corresponding to ventricular repolarization.) Hence, within the IEGM, an intrinsic cardiac cycle is deemed to extend from P-wave to P-wave. If the atria are paced, the paced cardiac cycle is deemed to extend from A-pulse to A-pulse. Within the PAP waveform, PAS typically occurs after the QRS and before the end of the T-wave. This pressure is at the peak of the PAP waveform. PAD/PAEDP occurs at the end of the R-wave where a sharp systolic upstroke begins. An ideal PAP waveform will have a smooth progressive diastolic runoff to end diastole and a smooth systolic upstroke. The PAEDP and the minimum PAD will thus be equal. The dicrotic notch occurs after the T-wave on the downstroke of the PA wave from pulmonic valve closure. Note that the ventricular depolarization observed within the ECG is typically referred to as a QRS-complex whereas the same event within the IEGM is referred to as the R-wave or "VS/VP".

Hence, if the PAP monitor is programmed to track PAD to PAD intervals within the PAP signal, the start and end points of this interval will not correspond to the start and end points of the cardiac cycle of the IEGM. Nevertheless, the durations of cardiac cycle intervals observed within the PAP signal will correspond to the durations of cardiac cycle intervals observed within an IEGM (or surface EKG) and so the PAP intervals may be reliably used to assess cardiac cycle stability. Note also that it is not necessary for each of the PAD, PAS and dicrotic notch features of the PAP signal shown in FIG. 5 to be individually identifiable within each waveform for the purposes of measuring waveform intervals to assess PAP interval stability, which should not be confused with the typical R-R interval stability assessment made by a CRMD. For example, it is not necessary that the dicrotic notch be identifiable in the signal, as it might be obscured by signal noise. Rather, it is sufficient that the system can reliably identify at least some fiducial points in the PAP signal (typically PAS or PAD) so that cardiac cycle intervals can be detected and tracked. For other purposes, the dicrotic notch may be advantageously detected, such as to measure and quantify morphology changes of the dicrotic notch over time for use in evaluating hemodynamic performance related to valve function, especially the pulmonic valve. (In this regard, although the PAP signal might not provide much information relating to the aortic valve, it could be used as an indicator of pulmonic valve function. In particular, any dramatic changes in amplitude or timing in reference to the PAS and PAD may indicate a change in valve function.) Returning to FIG. 4A, at step 310, for a given PAP interval that corresponds to the duration of a cardiac cycle (such as PAD-PAD intervals), the PAP monitor assesses interval stability by: identifying and rejecting the longest and shortest intervals, identifying and selecting the second longest and second shortest intervals, then determining the difference between the second longest and second shortest intervals for use a stability indicator. See, for example, difference-based techniques described in: U.S. Pat. No. 7,974,687 to Farazi et al. and in U.S. Pat. No. 8,249,707 of Nabutovsky et al. Additionally or alternatively, the system calculates an average PAP waveform interval stability value and compares it to a baseline PAP waveform interval stability to generate the stability indicator/score. In this regard, normally conducted ventricular beats will generate a stable PAP calculation indicating a similarity to the baseline PAP interval stability, thus not indicating a potential arrhythmia.

Figure 6:
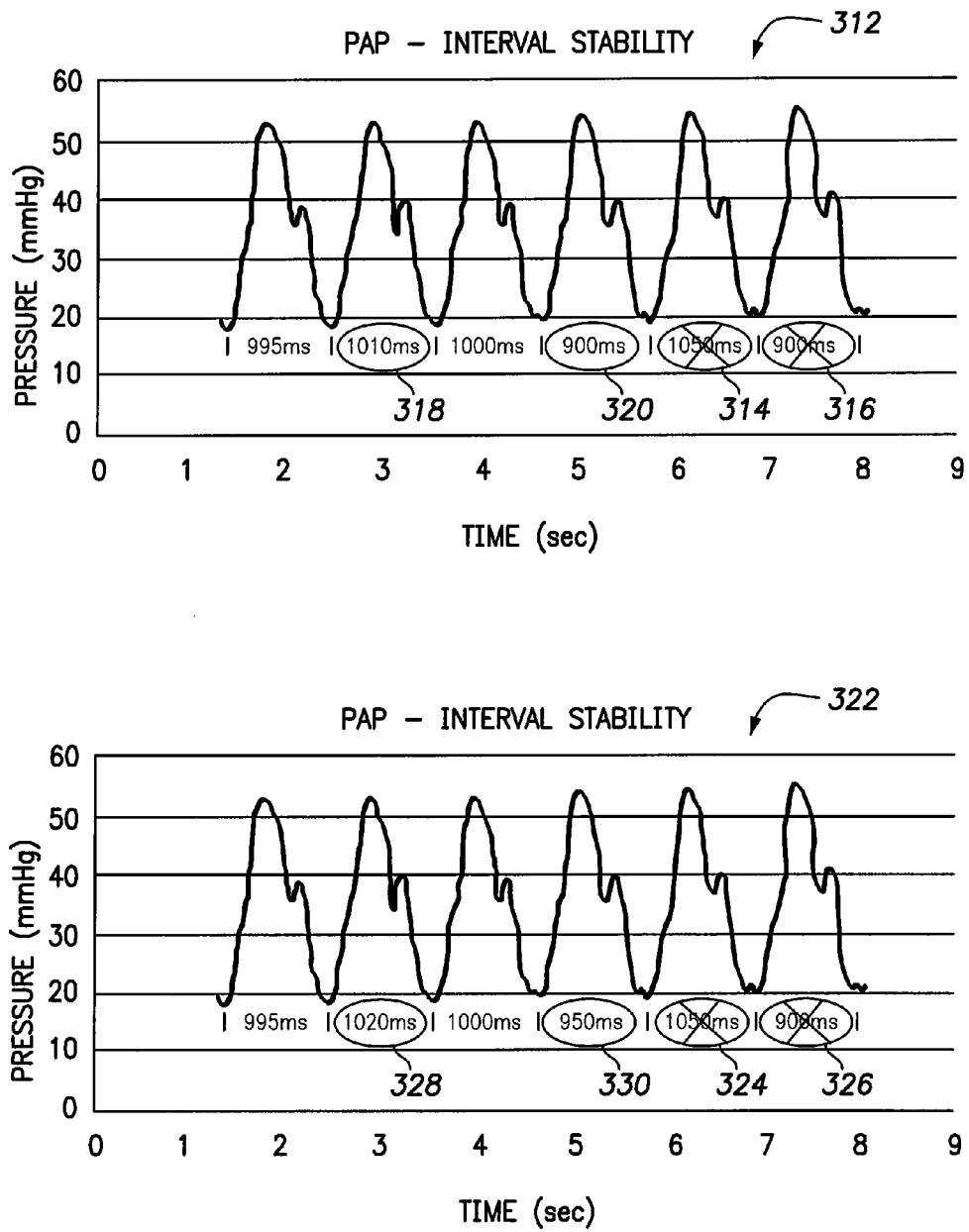
FIG. 6 graphically illustrates exemplary PAP waveforms that may be analyzed by the technique of FIGS. 4A and 4B, specifically highlighting differences in interval duration from which interval stability can be assessed.

FIG. 6 shows exemplary PAP signals illustrating stability assessment made based on PAD-PAD intervals. In the first graph 312, a set of PAD-PAD intervals are shown wherein the values are 995 milliseconds (ms), 1010 ms, 1000 ms, 990 ms, 1050 ms and 900 ms. Using the above-described procedure, the longest and shortest intervals are discarded (as indicated by crossed-out values 314 and 316) and the second longest and second shortest intervals are selected (as indicated by ovals 318 and 320) to determine interval stability. That is, in this example, the stability indicator is set to 1010 ms minus 990 ms or 20 ms. In the second graph 322, the interval values are 995 ms, 1020 ms, 1000 ms, 950 ms, 1050 ms and 900 ms. Again, the longest and shortest intervals are discarded (as indicated by crossed-out values 324 and 326) and the second longest and second shortest intervals are selected (as indicated by ovals 328 and 330) to determine interval stability. That is, in this second example, the stability indicator is set to 1020 ms minus 950 ms or 70 ms.

Figure 4B:
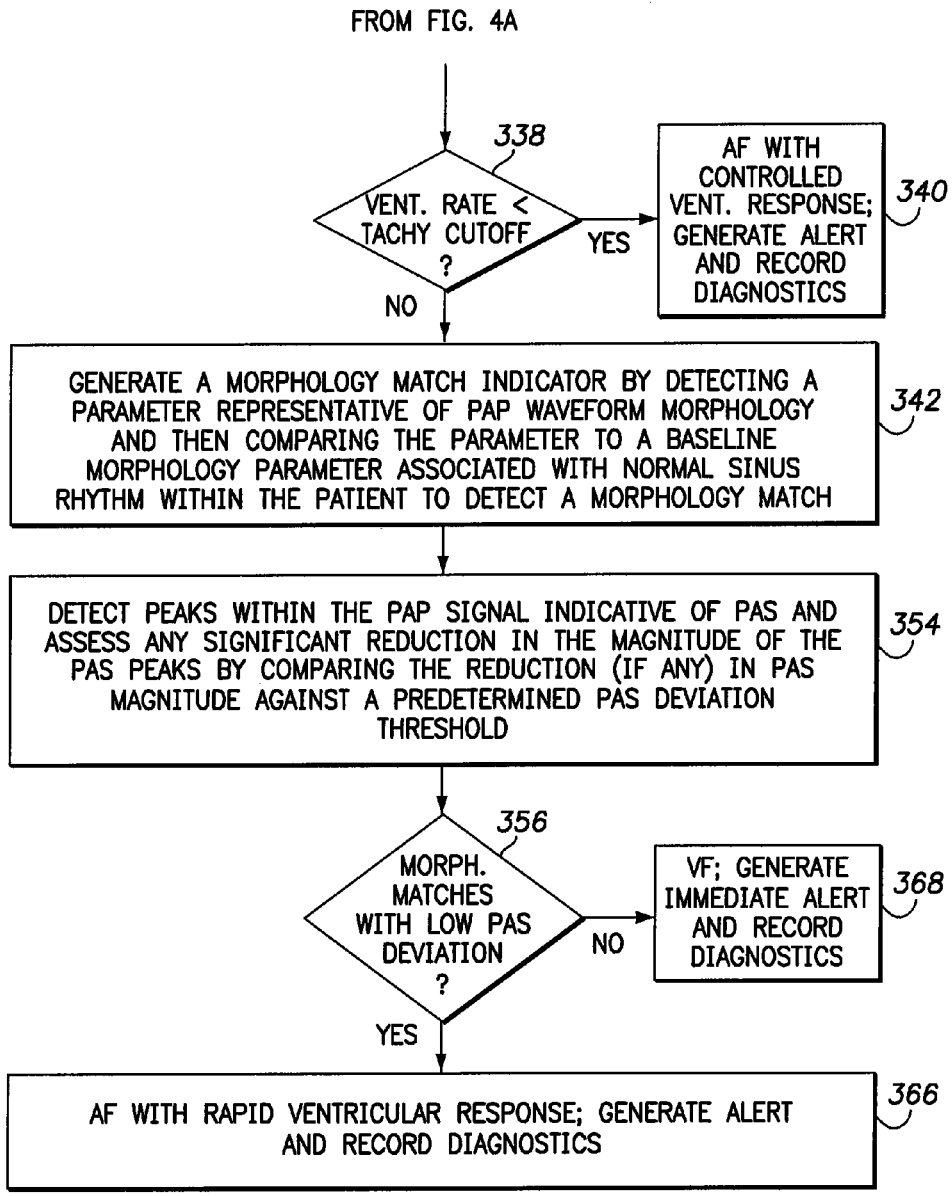

At step 332 of FIG. 4A, the PAP monitor compares the stability indicator to a stability criteria threshold set based on a preprogrammed value or a predetermined patient stability baseline (such as a threshold of 40 ms) or expressed as a predetermined percentage deviation from the baseline. If the indicator is found to be above the threshold at step 334 (indicating that the PAP signal is relatively instable or unstable), the PAP monitor then proceeds to step 336 to begin discriminating among different irregular cardiac rhythms. At step 336, the PAP monitor determines the current ventricular rate based on the duration of the intervals and compares the rate against a tachycardia rate threshold (or tachy cutoff). For example, an interval duration of 1000 ms corresponds to a rate of sixty beats per minute. The tachycardia threshold may be set, for example, to 140 beats per minute (bpm). Assuming the ventricular rate is below the tachy cutoff (as determined at decision step 338 of FIG. 4B), the PAP monitor thereby determines that the irregular rhythm is AF with controlled ventricular response and, at step 340, generates alerts or warnings and records diagnostics. The diagnostics may include the current PAP interval stability indicator value, a sample of the PAP waveform itself, as well as the current detection parameters such as the current values of the tachy threshold and the stability threshold.

Conversely, if the ventricular rate is found to be at or above the tachy cutoff (i.e. some form of tachycardia is indicated), the PAP monitor at step 342 begins procedures to distinguish AF with rapid ventricular response from VF. In this regard, tachycardias with a ventricular origin generate a high PAP stability score (i.e. low interval delta) indicating an independent high rate ventricular rhythm. However, AF with rapid ventricular conduction exhibits wide variations in the interval duration due to the erratic conduction from the atria and generates a low PAP stability score (i.e. high interval delta). To exploit this distinction, the PAP monitor at step 342 generates a morphology match indicator by detecting a parameter representative of the current PAP waveform morphology and then comparing the parameter to a predetermined baseline morphology parameter associated with normal sinus rhythm within the patient to detect a possible morphology match.

Figure 7:
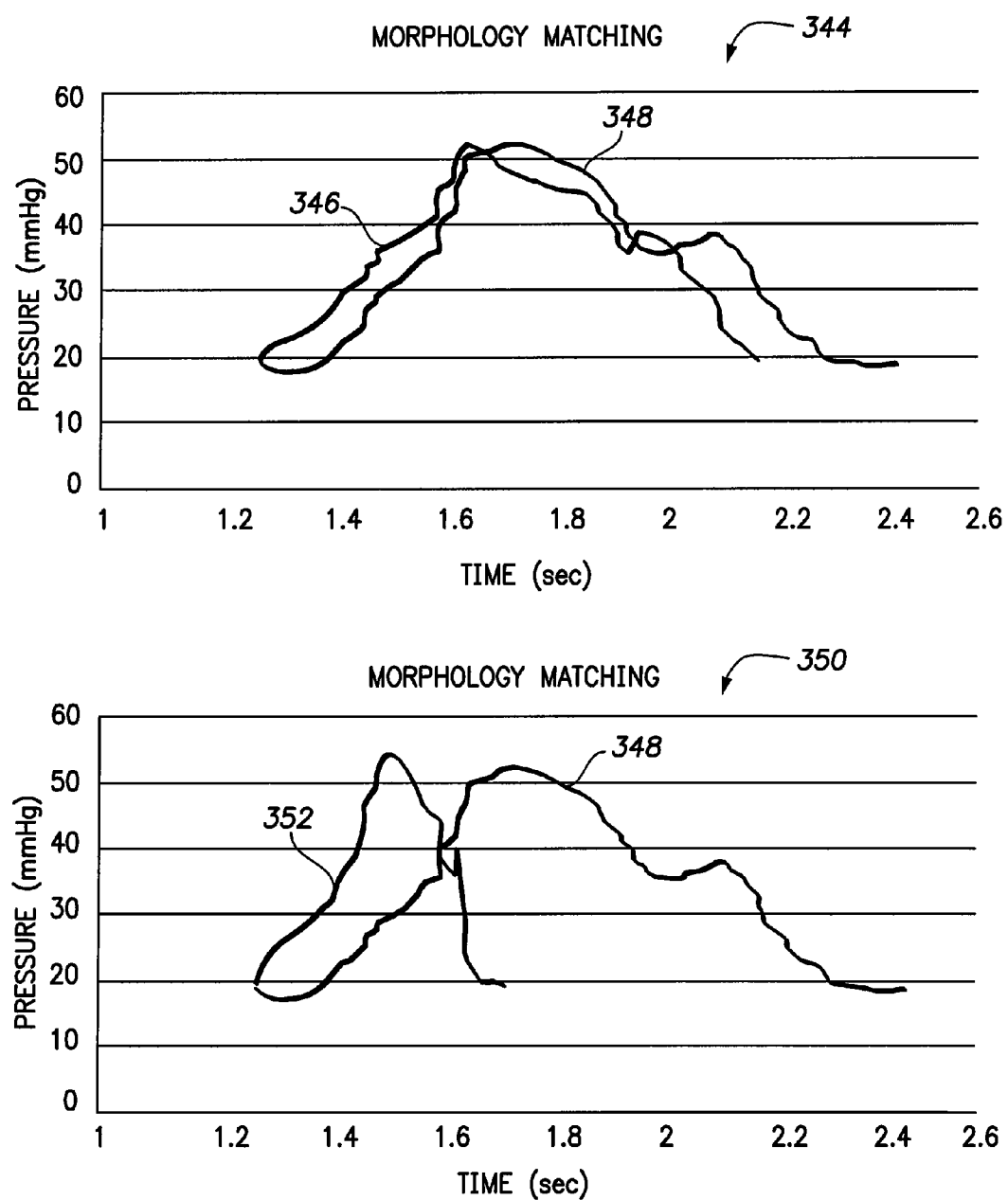
FIG. 7 graphically illustrates exemplary PAP waveforms that may be analyzed by the technique of FIGS. 4A and 4B, specifically highlighting differences in waveform morphology that can be used to discriminate certain arrhythmias.

FIG. 7 shows exemplary PAP signals to illustrate morphology matching. In the first graph 344, an exemplary PAP waveform 346 is compared to a baseline waveform 348 predetermined within the patient during normal sinus rhythm (as may be obtained during an initial programming session under clinician supervision) to determine the correlation there between. In this case, there is a strong correlation (with a coefficient of 0.80) indicating that the PAP waveform corresponds to a sinus rhythm waveform. As such, the cardiac rhythm is likely to be AF with rapid ventricular response. In the second graph 350, another exemplary PAP waveform 352 is compared to the baseline waveform 348. In this case, however, the correlation is poor (with a coefficient of −0.18) indicating that the PAP waveform does not correspond to sinus rhythm and may instead be a VF waveform.

Returning to FIG. 4B, at step 354 the PAP monitor then seeks to confirm or corroborate this determination based on a reduction (if any) within the amplitude of PAS peaks of the PAP signal. That is, at step 356, the PAP monitor detects peaks within the PAP signal indicative of PAS and assesses any significant reduction in the magnitude of the peaks (that may be associated with a loss of cardiac output due to fibrillation) by comparing the reduction (if any) in PAS magnitude against a predetermined PAS deviation threshold. The PAP monitor thereby generates a PAS peak indicator for comparison against a predetermined PAS deviation threshold that assesses whether the PAS peaks are relatively consistent or inconsistent. It is noted that inconsistent PAS peaks might be indicative of AF and so a PAP waveform morphology template may be stored for further analysis or clinician review. That is, there will be some irregularity of PAS peaks with AF. (The PAS peak consistency indicator value may be evaluated relative to an AF range.) The various analysis options (stability, morphology, PAS peaks, etc.) of the system are preferably programmed such that the options can be turned off or set to passive if not helpful in a specific clinical situation.

At step 356, the PAP monitor compares the morphology match indicator against a suitable morphology threshold while also comparing the PAS deviation indicator against a suitable deviation threshold. Then, if waveform morphology adequately matches sinus rhythm morphology and the PAS reduction (if any) is relatively low, the irregular cardiac rhythm is identified as AF with rapid ventricular response at step 366 and suitable actions are taken, such as generating warnings to alert the clinician or caregiver and recording appropriate diagnostics. If the waveform morphology fails to adequately match sinus rhythm morphology and the PAS is significantly reduced, the irregular cardiac rhythm is deemed to be a possible VF at step 368 and emergency actions are taken, such as generating warnings to alert emergency personnel and recording appropriate diagnostics. Note that if the morphology match is relatively good but the PAS reduction is large, or the morphology match is poor but the PAS deviation is small, then the result of the discrimination at step 356 may be ambiguous. Depending upon device programming, the PAP monitor may then generate warnings to indicate that some form of high rate irregular rhythm has been detected. In this regard, a relatively good morphology match coupled with a large PAS reduction might correlate to pumping inefficiencies or weaker cardiac contractions. Conversely, a poor morphology match coupled with a small PAS deviation is probably an ambiguous result. Hence, a reduced PAS indicates a cardiac concern, which may depend on the particular rate branch it is in and the stability indication. Hence, preferably, the system is equipped such that the clinician can turn on/off certain discriminators. Note also that, when implementing the method with the system of FIG. 2, there is clinical value in assisting the ICD with VF confirmation, which ultimately leads to the emergency action of delivering high voltage therapy to convert the VF back to sinus rhythm.

As already explained, if the PAP monitor is a component of a CRMD, the device will primarily use IEGM signals to detect and discriminate irregular cardiac rhythms but the PAP-based techniques described herein may be used to corroborate that determination while also providing additional PAP-based diagnostic data. For implementations where the PAP monitor is an external system that receives PAP signals wirelessly from the implanted PAP sensor, the patient may be instructed to activate the system whenever an arrhythmia is suspected so that the PAP monitor can then attempt to discriminate the arrhythmia (if any) based on the PAP signals and relay the resulting information to the clinician or caregiver for review. (It is noted that, if the patient is suffering an episode of VF, activation of an external PAP monitor is not warranted and immediate delivery of defibrillation shocks by caregivers or family members is instead advised.)

Figure 8:
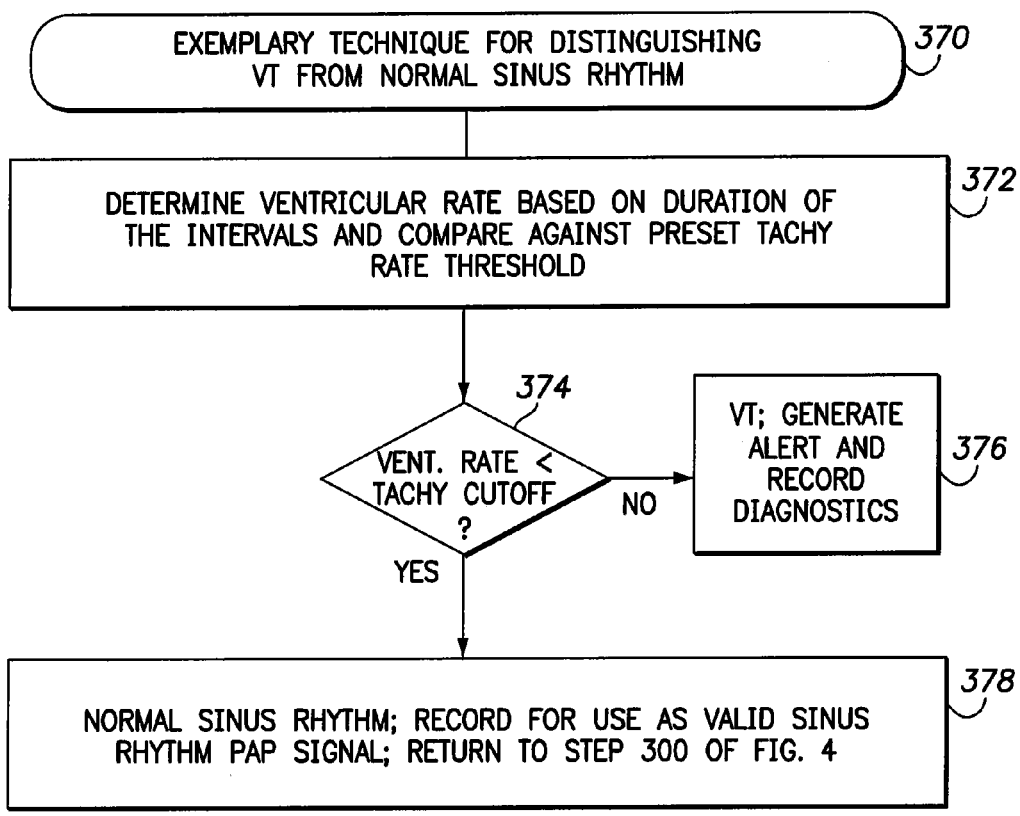
FIG. 8 illustrates an exemplary technique for use with the method of FIG. 4 for discriminating VT from normal sinus rhythm.

If the PAP signal was initially found to be stable at step 334, the PAP monitor then proceeds to step 370 to distinguish VT from normal sinus rhythm using the procedures of FIG. 8. At step 372 of FIG. 8, the PAP monitor determines the ventricular rate based on the duration of the intervals and compares it against the preset tachycardia rate threshold (which may be set to 140 bpm as discussed above.) If the rate exceeds the threshold at step 374, VT is thereby indicated and the PAP monitor at step 376 generates alerts and records diagnostics. Otherwise, the PAP signal is deemed to correspond to a normal sinus rhythm. The PAP monitor may then record the latest PAP signal data for use in updating baseline values or the like. Although not explicitly shown, following steps 370, 340 or 368 of FIGS. 4A and 4B, processing returns to step 300 so that the PAP monitor may sense and analyze additional PAP signals.

Figure 9:
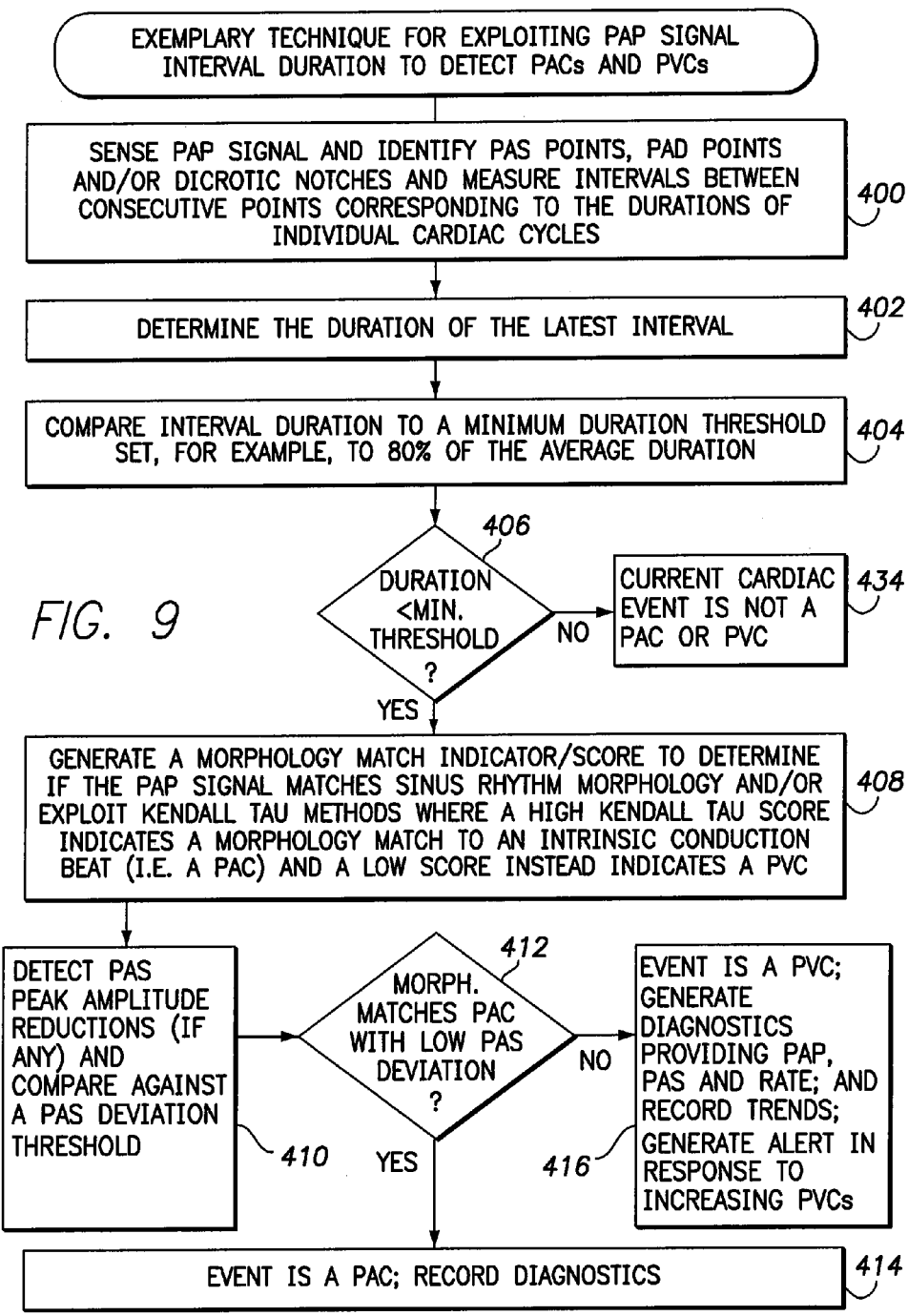
FIG. 9 illustrates an exemplary technique for use with the general method of FIG. 3, wherein the durations of PAP intervals are exploited to detect and discriminate PACs and PVCs.

Turning next to FIG. 9, exemplary techniques for exploiting PAP interval durations to detect PACs and PVCs will be described. Some of the steps are the same or similar to those described above and hence will not be described again in detail. At step 400, the PAP monitor senses the PAP signal and identifies PAS points, PAD points, dicrotic notches or other fiducial points and measures intervals between consecutive points corresponding to the durations of individual cardiac cycles. At step 402, the PAP monitor determines the duration of the latest interval. Exemplary intervals are shown in FIG. 6, discussed above. At step 404, the PAP monitor compares the interval duration to a minimum duration threshold set, for example, to 80% of the average interval duration determined based on the most recent set of PAP intervals. If the interval duration is found to be less than the threshold at step 406 (indicating that the current cardiac cycle is likely a premature contraction), the PAP monitor then proceeds to step 408 to begin discriminating PAC from PVC.

At step 408, the PAP monitor generates a morphology match indicator to determine if the PAP signal corresponding to the short cardiac matches a normal sinus rhythm morphology. This may be performed as described above. If the morphology match indicates that the PAP waveform corresponds to a sinus rhythm waveform, the short cardiac cycle is likely a PAC (since, even with a PAC, there is regular conduction to the ventricles and so the PAP waveform will generally correspond to sinus rhythm morphology.) Conversely, if there is a poor morphology match with the sinus rhythm waveform, the short cardiac cycle is likely a PVC (since PVCs are triggered by irregular conduction and so the PAP waveform will not likely match sinus rhythm morphology.) Additionally or alternatively, the PAP monitor may exploit kendall tau methods where a high kendall tau score indicates a match to an intrinsic conduction beat (PAC) and a low score instead indicates a PVC. Kendall tau methods are discussed in U.S. Pat. No. 7,706,865 to Snell and in U.S. Pat. No. 8,126,552 to Min et al. and U.S. Published Patent Application No. 2010/0114228 to Bharmi et al.

At step 410, the PAP monitor seeks to confirm or corroborate this determination based on reductions (if any) within the PAS peaks of the PAP signal. That is, at step 410, the PAP monitor detects peaks within the PAP signal indicative of PAS and assesses any significant reduction in the magnitude of the peaks by comparing the reduction against a predetermined PAS deviation threshold, as discussed above. Hence, the PAP monitor generates a PAS peak consistency indicator for comparison against a predetermined PAS deviation threshold. In this regard, PACs should maintain PAS amplitude within a set deviation or percentage from average. If the PAS amplitude falls outside of that window, the event is likely to be a PVC.

At step 412, the PAP monitor compares the morphology match indicator against a suitable morphology match threshold while also comparing the PAS deviation indicator against a suitable deviation threshold. Then, if waveform morphology adequately matches sinus rhythm morphology (and/or there is a high kendall tau score) and the PAS peak reduction (if any) is relatively low, the premature beat is confirmed as a PAC at step 414 and suitable diagnostics are recorded. If the waveform morphology fails to adequately match sinus rhythm morphology (and/or there is a low kendall tau score) and the PAS peak reduction are relatively high, the premature beat is deemed to be a PVC at step 416 and suitable diagnostics are recorded. Since PVCs can be more problematic than PACs, a greater amount of diagnostic information may be recorded in response to the PVC, such as a recording of PAP signal corresponding to the PVC, the PAS values, the ventricular rate, etc. Trends in these values may be tracked and recorded as well, with warnings generated if there is a significant increase in PVCs (e.g. if a count of PVCs exceeds an acceptable amount.)

Note that if the morphology match is relatively good but the PAS reduction is large, or the morphology match is poor but the PAS deviation is small, then the discrimination of step 412 is ambiguous or may be indicative of a cardiac concern as discussed above. That is, a relatively good morphology match coupled with a large PAS reduction might correlate to pumping inefficiencies or weaker cardiac contractions and might also indicate a co-morbidity such as volume under load. Depending upon device programming, the PAP monitor may then record diagnostics to indicate that some form of premature contractions have been detected. If the PAP monitor is a component of a CRMD, the device will primarily use IEGM signals to detect and discriminate premature contractions, but the PAP-based techniques described herein may be used to corroborate that determination while also providing additional PAP-based diagnostic data for subsequent clinician review. Note that if the duration of the PAP interval was found to be at or above the minimum threshold at step 406, the PAP monitor concludes at step 434 that the latest cardiac cycle is not a premature contraction. Although not explicitly shown, following steps 414, 416 or 434, processing returns to step 400 so that the PAP monitor may sense and analyze additional PAP signals.

What have been described thus far are PAP-based techniques for detecting and discriminating irregular cardiac rhythms. If the system is equipped to measure LAP (either directly or using a proxy for LAP), the aforementioned PAP-based techniques can be extended or modified to evaluate irregular cardiac rhythms based on LAP. Generally speaking, the above-described methods are modified to use the atrial and ventricular components of the LAP waveform, or additional LAP-based techniques are provided for which the PAP signal may not be well suited. Moreover, rather than using interval stability for AF detection, the system leverages morphology matching or exploits rate as an indicator for a high atrial rate. Exemplary LAP-based techniques are described in the next section.

LAP-Based Techniques for Detecting Irregular Cardiac Rhythms

Figure 10:
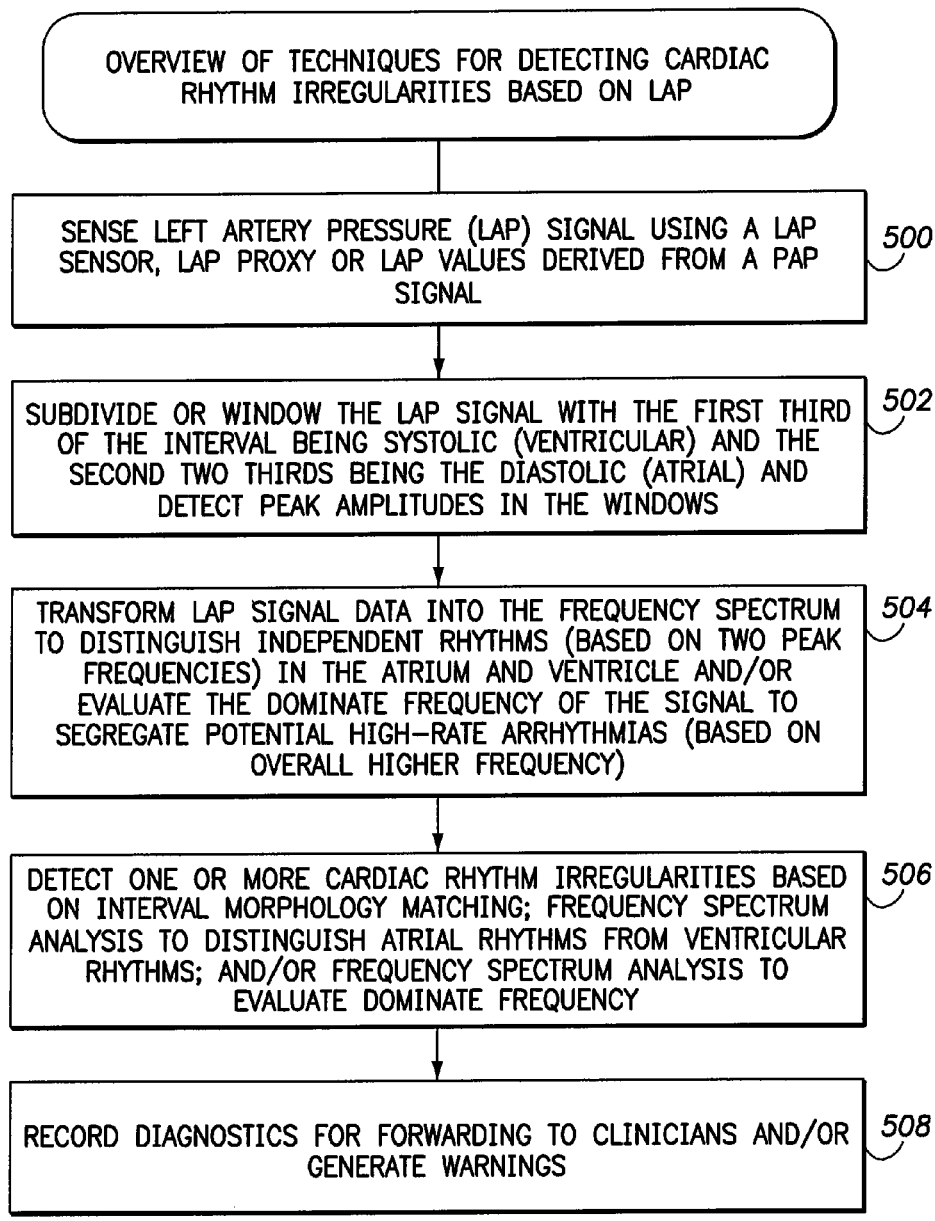
FIG. 10 illustrates an exemplary technique for use with the general method of FIG. 3, wherein LAP signals are additionally or alternatively exploited.

FIG. 10 broadly summarizes techniques exploited by suitably-equipped implantable medical systems for detecting and discriminating irregular cardiac rhythms based on LAP. Briefly, at step 500, the system senses time-varying LAP signals using an implanted LAP sensor, obtains LAP values using a suitable proxy, or derives LAP from the PAP signal. In particular, with the PAP sensor implanted as shown in FIG. 1, LAP data can be derived from the PAP signal since PAP is correlated to LAP, with the main difference being the gradient across the lungs and pulmonary veins. As such, the range of the PAP waveform does not drop to the typical diastolic pressures of the RV but maintains a slightly higher diastolic pressure level such as seen in the left atrium. Hence, in at least some embodiments, data obtained from the PAP sensor serves as a source for LAP values, particularly if no other source of LAP data is available such as an LAP sensor.

LAP sensors are discussed in, for example, U.S. Pat. No. 7,115,095, of Eigler et al., entitled "Permanently Implantable System and Method for Detecting, Diagnosing and Treating Congestive Heart Failure." Other techniques for detecting LAP that do not necessarily require an LAP sensor (such as by using cardiogenic impedance as a proxy) are discussed in U.S. Provisional Patent Application No. 60/787,884 of Wong et al., entitled, "Tissue Characterization Using Intracardiac Impedances with an Implantable Lead System," filed Mar. 31, 2006, and in U.S. patent application Ser. Nos. 11/558,101; 11/557,851; 11/557,870; 11/557,882; and 11/558,088, each entitled "Systems and Methods to Monitor and Treat Heart Failure Conditions," of Panescu et al. See, also, U.S. patent application Ser. No. 11/558,194, by Panescu et al., entitled "Closed-Loop Adaptive Adjustment of Pacing Therapy Based on Cardiogenic Impedance Signals Detected by an Implantable Medical Device." See, also, U.S. patent application Ser. Nos. 11/779,350 and 11/779,380, of Wenzel et al., filed Jul. 18, 2007, both entitled "System and Method for Estimating Cardiac Pressure based on Cardiac Electrical Conduction delays using an Implantable Medical Device." See, also, U.S. patent application Ser. No. 11/856,443, filed Sep. 17, 2007, of Zhao et al., entitled "MEMS-Based Left Atrial Pressure Sensor for use with an Implantable Medical Device."

At step 502, the system subdivides or windows the LAP signal with the first third of the interval being systolic (ventricular) and the second two-thirds being the diastolic (atrial) and detects peak amplitudes in the windows. At step 504, the system also transforms the LAP signal data into the frequency spectrum (using any suitable conversion process such as a Fast Fourier Transform (FFT)) to distinguish independent rhythms (based on two peak frequencies) in the atrium and ventricle and/or the device evaluates the dominate frequency of the signal to segregate potential high-rate arrhythmias (based on overall higher frequency.) At step 506, the system then detects one or more cardiac rhythm irregularities based on interval morphology matching; frequency spectrum analysis (or waveform stability) to distinguish atrial rhythms from ventricular rhythms; and/or frequency spectrum analysis to evaluate dominate frequency.

For example, using the LAP alongside with the IEGM provides both ventricular (V wave on LAP) and atrial (IEGM) components to assess overall correlation between atrial and ventricular function to potentially distinguish certain cardiac arrhythmias. For instance, using the atrial IEGM, the system may determine the atrial rate and then using the LAP waveform (ventricular peak), the system may determine the ventricular rate. Comparing these two rates then allows the system to group the arrhythmia into specific comparative rate bins (V=A, V>A, V<A). In each specific bin additional analysis may be performed by the system. In general, V>A=VF. However, where V=A if the information is available the system may examine the onset of the arrhythmia (if slow then SVT and if abrupt VT), and where V<A, the system may examine the correlation of the A and V events (if strong correlation VT and if not AF w/RVR). Moreover, the system may incorporate procedures to confirm A, C, V components using the IEGM (i.e. if a component <50 ms from IEGM then it is considered an A event) or detection of a dLAP/dt downslope may be used confirm events that are truly ventricular. In the LAP waveform, the ventricular and atrial upslopes may be relatively similar, however, the ventricular downslope is very distinct in comparison to the atrial component. At step 508, depending upon the irregular cardiac rhythm detected (if any), alerts are generated and diagnostics recorded.

Note that at least some of these LAP-based applications might be performed using a PAP signal. However, the use of a PAP signal may be more difficult for these applications because of the physical separation of the pressure transducer placement providing a much reduced signal resolution (and potentially some LAP signal attenuation by time it is read in the PA.) In addition, the RV pressure in comparison is so much higher that it may be difficult to separate the two components. The LAP signal however has very distinct A, C, V (atrial contraction, valve closure, and mitral bulging from ventricular contraction) components, which can be advantageously exploited.

For the sake of completeness, an exemplary CRMD will now be described for use with embodiments where the PAP monitor is a feature or component of the CRMD.

Exemplary CRMD with on-Board PAP Monitor

Figure 11:
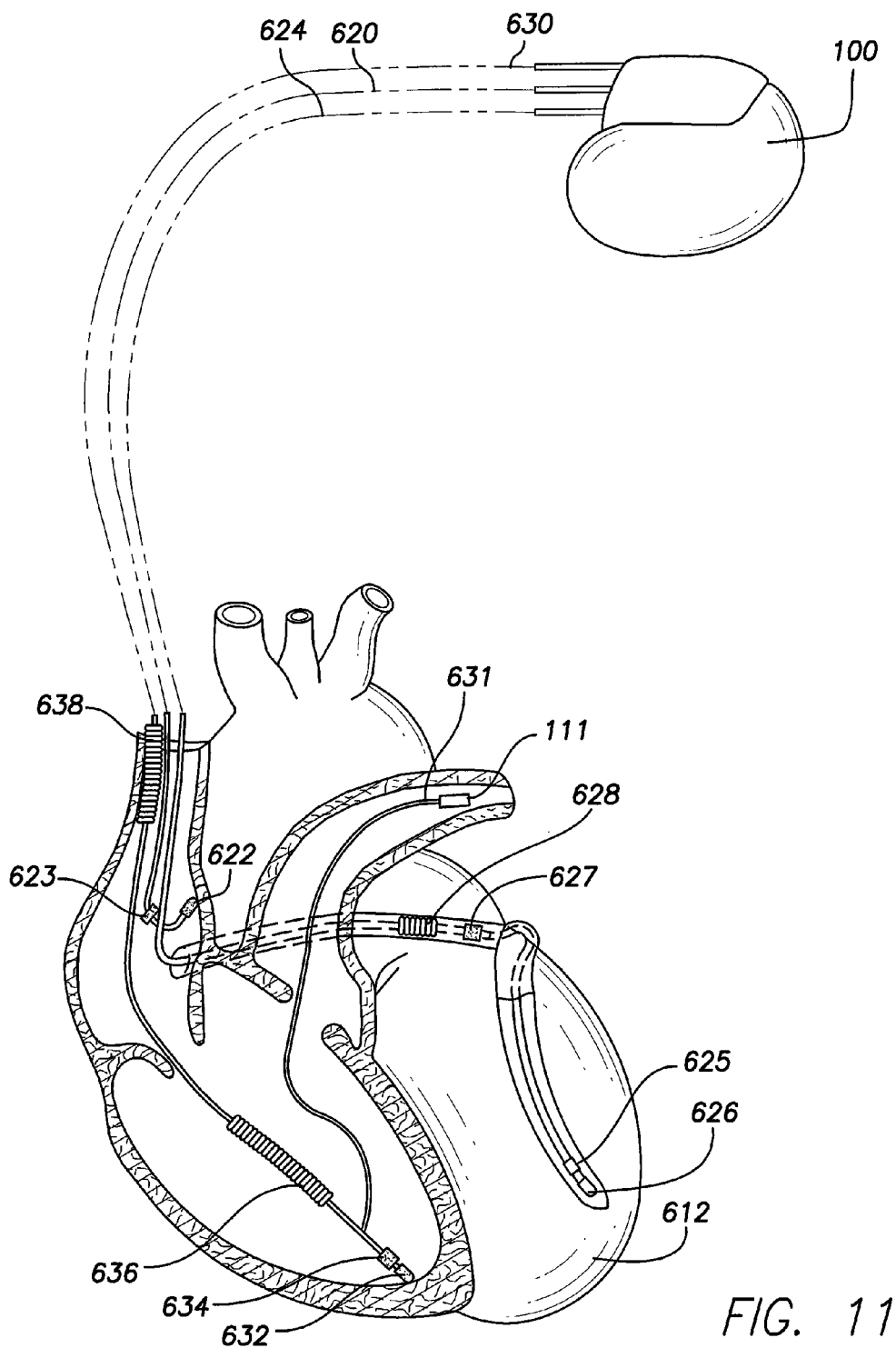
FIG. 11 is a simplified, partly cutaway view, illustrating the CRMD of FIG. 2 along with at set of leads implanted in or on the heart of the patient.
Figure 12:
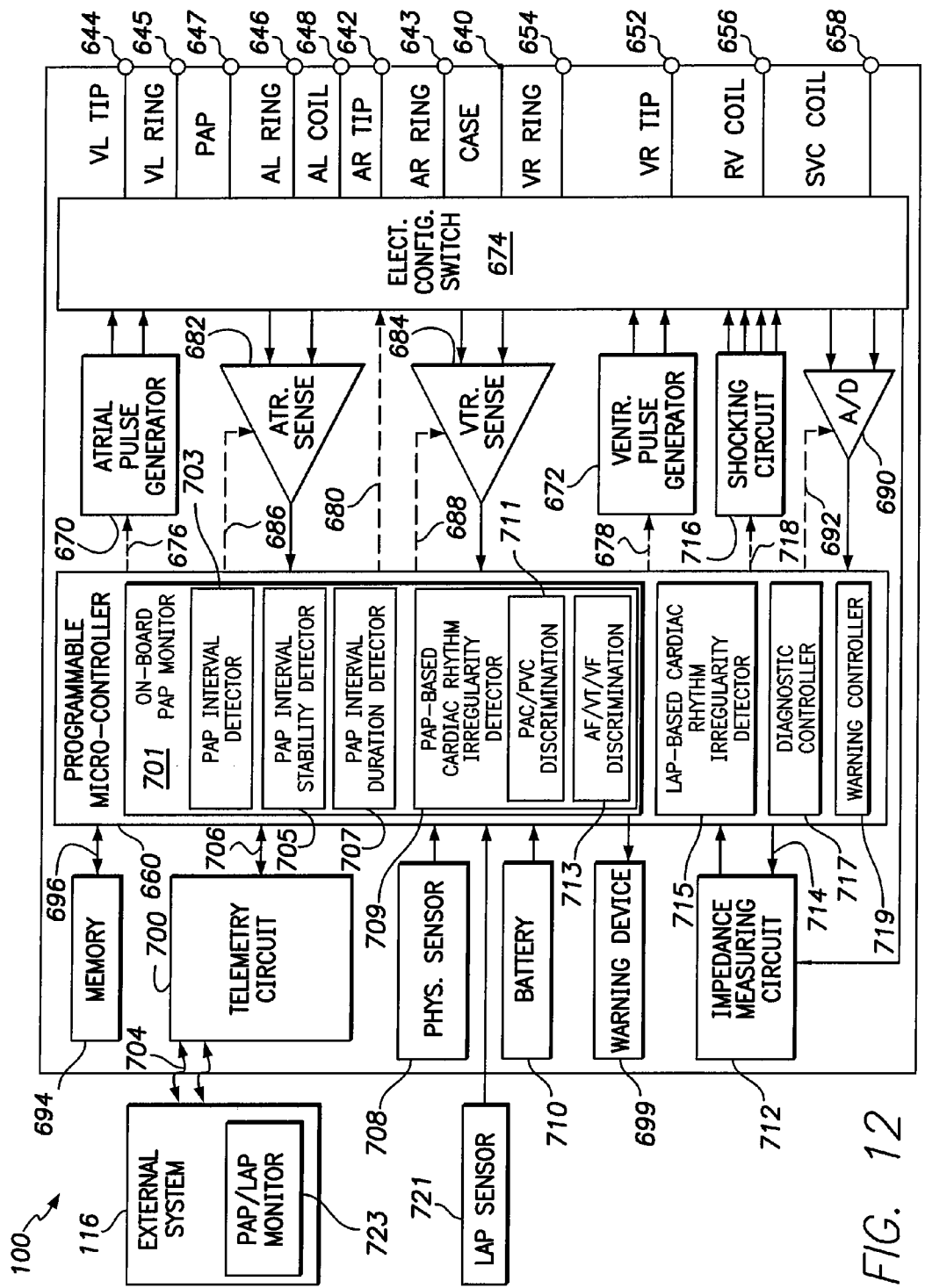
FIG. 12 is a functional block diagram of the CRMD of FIG. 11, illustrating basic circuit elements that provide cardioversion, defibrillation and/or pacing stimulation in the heart and particularly illustrating components of an on-board PAP monitor.

With reference to FIGS. 11 and 12, an exemplary CRMD will now be described where the CRMD is equipped with an on-board PAP monitor. FIG. 11 provides a simplified block diagram of the CRMD, which is a dual-chamber stimulation device capable of treating both fast and slow arrhythmias with stimulation therapy, including cardioversion, defibrillation and pacing stimulation. To provide atrial chamber pacing stimulation and sensing, CRMD 100 is in electrical communication with a heart 612 by way of a left atrial lead 620 having an atrial tip electrode 622 and an atrial ring electrode 623 implanted in the atrial appendage. CRMD 100 is also in electrical communication with the heart by way of a right ventricular lead 630 having, in this embodiment, a ventricular tip electrode 632, a right ventricular ring electrode 634, a right ventricular (RV) coil electrode 636, and a superior vena cava (SVC) coil electrode 638. The SVC coil electrode, as with many lead components, is optional. Typically, the right ventricular lead 630 is transvenously inserted into the heart so as to place the RV coil electrode 636 in the right ventricular apex, and the SVC coil electrode 638 in the superior vena cava. Accordingly, the right ventricular lead is capable of receiving cardiac signals, and delivering stimulation in the form of pacing and shock therapy to the right ventricle.

Right ventricular lead 630 also includes a pulmonary artery extension 631 equipped with a PA sensor 111. In one example, the pulmonary artery extension 631 is sized, shaped and configured to position the sensor in the pulmonary artery as shown. In other examples, it is located above the RV coil (and below the tricuspid valve.) Signals representative of PAP are routed back along pulmonary artery extension 631 to the main portion of lead 630 and then to the CRMD for processing. This is just one example of a PAP sensor arrangement. See, also, sensors described in U.S. patent application Ser. No. 11/927,026, filed Oct. 29, 2007, of Nabutovsky et al., entitled "Systems and Methods for Exploiting Venous Blood Oxygen Saturation in Combination with Hematocrit or other Sensor Parameters for use with an Implantable Medical Device."

To sense left atrial and ventricular cardiac signals and to provide left chamber pacing therapy, CRMD 100 is coupled to an LV lead 624 designed for placement in the "CS region" via the CS os for positioning a distal electrode adjacent to the left ventricle and/or additional electrode(s) adjacent to the left atrium. As used herein, the phrase "CS region" refers to the venous vasculature of the left ventricle, including any portion of the CS, great cardiac vein, left marginal vein, left posterior ventricular vein, middle cardiac vein, and/or small cardiac vein or any other cardiac vein accessible by the CS. Accordingly, the exemplary LV lead 624 is designed to receive atrial and ventricular cardiac signals and to deliver left ventricular pacing therapy using a pair of tip and ring electrodes 625 and 626, left atrial pacing therapy using at least a left atrial ring electrode 627, and shocking therapy using at least a left atrial coil electrode 628. In other examples, more or fewer LV electrodes are provided. Although only three leads are shown in FIG. 11, it should also be understood that additional leads (with one or more pacing, sensing and/or shocking electrodes) might be used and/or additional electrodes might be provided on the leads already shown, such as additional electrodes on the RV lead. Note that, on present commercially-available hardware, there is often no separate electrode 627.

A simplified block diagram of internal components of CRMD 100 is shown in FIG. 12. While a particular CRMD is shown, this is for illustrative purposes only, and one of skill in the art could readily duplicate, eliminate or disable the appropriate circuitry in any desired combination to provide a device capable of treating the appropriate chamber(s) with cardioversion, defibrillation and pacing stimulation. The housing 640 for CRMD 100, shown schematically in FIG. 12, is often referred to as the "can", "case" or "case electrode" and may be programmably selected to act as the return electrode for all "unipolar" modes. The housing 640 may further be used as a return electrode alone or in combination with one or more of the coil electrodes, 628, 636 and 638, for shocking purposes. The housing 640 further includes a connector (not shown) having a plurality of terminals, 642, 643, 644, 645, 646, 648, 652, 654, 656 and 658 (shown schematically and, for convenience, the names of the electrodes to which they are connected are shown next to the terminals). As such, to achieve right atrial sensing and pacing, the connector includes at least a right atrial tip terminal ($A_R$ TIP) 642 adapted for connection to the atrial tip electrode 622 and a right atrial ring ($A_R$ RING) electrode 643 adapted for connection to right atrial ring electrode 623. To achieve left chamber sensing and pacing, the connector includes, at least, left ventricular tip and ring terminals 644 and 645, respectively. Additionally, a PAP terminal 647 is provided for receiving signals from PAP sensor 111 (FIG. 2.) If a separate LAP sensor is provided, an additional terminal may be needed. Within the figure, an LAP sensor 721 is shown schematically.

The connector also includes a left atrial ring terminal ($A_L$ RING) 646 and a left atrial shocking terminal ($A_L$ COIL) 648, which are adapted for connection to the left atrial ring electrode 627 and the left atrial coil electrode 628, respectively. To support right chamber sensing, pacing and shocking, the connector further includes a right ventricular tip terminal ($V_R$ TIP) 652, a right ventricular ring terminal ($V_R$ RING) 654, a right ventricular shocking terminal (RV COIL) 656, and an SVC shocking terminal (SVC COIL) 658, which are adapted for connection to the RV tip electrode 632, right ventricular ring electrode 634, the $V_R$ coil electrode 636, and the SVC coil electrode 638, respectively.

At the core of CRMD 100 is a programmable microcontroller 660, which controls the various modes of stimulation therapy. As is well known in the art, the microcontroller 660 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 660 includes the ability to process or monitor input signals (data) as controlled by a program code stored in a designated block of memory. The details of the design and operation of the microcontroller 660 are not critical to the invention. Rather, any suitable microcontroller 660 may be used that carries out the functions described herein. The use of microprocessor-based control circuits for performing timing and data analysis functions are well known in the art.

As shown in FIG. 12, an atrial pulse generator 670 and a ventricular pulse generator 672 generate pacing stimulation pulses for delivery by the right atrial lead 620, the right ventricular lead 630, and/or the LV lead 624 via an electrode configuration switch 674. It is understood that in order to provide stimulation therapy in each of the four chambers of the heart, the atrial and ventricular pulse generators, 670 and 672, may include dedicated, independent pulse generators, multiplexed pulse generators or shared pulse generators. The pulse generators, 670 and 672, are controlled by the microcontroller 660 via appropriate control signals, 676 and 678, respectively, to trigger or inhibit the stimulation pulses.

The microcontroller 660 further includes timing control circuitry (not separately shown) used to control the timing of such stimulation pulses (e.g., pacing rate, AV delay, atrial interconduction (inter-atrial) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 674 includes a plurality of switches for connecting the desired electrodes to the appropriate I/O circuits, thereby providing complete electrode programmability. Accordingly, the switch 674, in response to a control signal 680 from the microcontroller 660, determines the polarity of the stimulation pulses (e.g., unipolar, bipolar, combipolar, etc.) by selectively closing the appropriate combination of switches (not shown) as is known in the art. The switch also switches among the various LV electrodes.

Atrial sensing circuits 682 and ventricular sensing circuits 684 may also be selectively coupled to the right atrial lead 620, LV lead 624, and the right ventricular lead 630, through the switch 674 for detecting the presence of cardiac activity in each of the four chambers of the heart. Accordingly, the atrial (ATR. SENSE) and ventricular (VTR. SENSE) sensing circuits, 682 and 684, may include dedicated sense amplifiers, multiplexed amplifiers or shared amplifiers. The switch 674 determines the "sensing polarity" of the cardiac signal by selectively closing the appropriate switches, as is also known in the art. In this way, the clinician may program the sensing polarity independent of the stimulation polarity. Each sensing circuit, 682 and 684, preferably employs one or more low power, precision amplifiers with programmable gain and/or automatic gain control, bandpass filtering, and a threshold detection circuit, as known in the art, to selectively sense the cardiac signal of interest. The automatic gain control enables CRMD 100 to deal effectively with the difficult problem of sensing the low amplitude signal characteristics of atrial or ventricular fibrillation. The outputs of the atrial and ventricular sensing circuits, 682 and 684, are connected to the microcontroller 660 which, in turn, are able to trigger or inhibit the atrial and ventricular pulse generators, 670 and 672, respectively, in a demand fashion in response to the absence or presence of cardiac activity in the appropriate chambers of the heart.

For IEGM-based arrhythmia detection, CRMD 100 utilizes the atrial and ventricular sensing circuits, 682 and 684, to sense cardiac signals to determine whether a rhythm is physiologic or pathologic. As used in this section "sensing" is reserved for the noting of an electrical signal, and "detection" is the processing of these sensed signals and noting the presence of an arrhythmia. The timing intervals between sensed events (e.g., AS, VS, and depolarization signals associated with fibrillation which are sometimes referred to as "F-waves" or "Fib-waves") are then classified by the microcontroller 660 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks). As already explained, various irregular cardiac rhythms can also be detected based on PAP or LAP signals and components for controlling those functions are described below.

Cardiac signals are also applied to the inputs of an analog-to-digital (A/D) data acquisition system 690. The data acquisition system 690 is configured to acquire the IEGM signals, convert the raw analog data into a digital signal, and store the digital signals for later processing and/or telemetric transmission to an external device 16. The data acquisition system 690 is coupled to the right atrial lead 620, the LV lead 624, and the right ventricular lead 630 through the switch 674 to sample cardiac signals across any pair of desired electrodes. The microcontroller 660 is further coupled to a memory 694 by a suitable data/address bus 696, wherein the programmable operating parameters used by the microcontroller 660 are stored and modified, as required, in order to customize the operation of CRMD 100 to suit the needs of a particular patient. Such operating parameters define, for example, the amplitude or magnitude, pulse duration, electrode polarity, for both pacing pulses and impedance detection pulses as well as pacing rate, sensitivity, arrhythmia detection criteria, and the amplitude, waveshape and vector of each shocking pulse to be delivered to the patient's heart within each respective tier of therapy. Other pacing parameters include base rate, rest rate and circadian base rate.

Advantageously, the operating parameters of the implantable CRMD 100 may be non-invasively programmed into the memory 694 through a telemetry circuit 700 in telemetric communication with the external device 116, such as a programmer, transtelephonic transceiver or a diagnostic system analyzer. The telemetry circuit 700 is activated by the microcontroller by a control signal 706. The telemetry circuit 700 advantageously allows intracardiac electrograms and status information relating to the operation of CRMD 1000 (as contained in the microcontroller 660 or memory 694) to be sent to the external device 116 through an established communication link 704. CRMD 100 further includes an accelerometer or other physiologic sensor 708, commonly referred to as a "rate-responsive" sensor because it is typically used to adjust pacing stimulation rate according to the exercise state of the patient. However, the physiological sensor 708 may further be used to detect changes in cardiac output, changes in the physiological condition of the heart, or diurnal changes in activity (e.g., detecting sleep and wake states) and to detect arousal from sleep. Accordingly, the microcontroller 660 responds by adjusting the various pacing parameters (such as rate, AV delay, VV delay, etc.) at which the atrial and ventricular pulse generators, 670 and 672, generate stimulation pulses. While shown as being included within CRMD 100, it is to be understood that the physiologic sensor 708 may also be external to CRMD 100, yet still be implanted within or carried by the patient. A common type of rate responsive sensor is an activity sensor incorporating an accelerometer or a piezoelectric crystal, which is mounted within the housing 640 of CRMD 100. Other types of physiologic sensors are also known, for example, sensors that sense the oxygen content of blood, respiration rate and/or minute ventilation, pH of blood, ventricular gradient, contractility, mechanical dyssynchrony, electrical dyssynchrony, photoplethysmography (PPG), LAP, heart sounds, etc.

The CRMD additionally includes a battery 710, which provides operating power to all of the circuits shown in FIG. 12. The battery 710 may vary depending on the capabilities of CRMD 100. If the system only provides low voltage therapy, a lithium iodine or lithium copper fluoride cell typically may be utilized. For CRMD 100, which employs shocking therapy, the battery 710 should be capable of operating at low current drains for long periods, and then be capable of providing high-current pulses (for capacitor charging) when the patient requires a shock pulse. The battery 710 should also have a predictable discharge characteristic so that elective replacement time can be detected. Accordingly, appropriate batteries are employed.

As further shown in FIG. 12, CRMD 100 has an impedance measuring circuit 712, enabled by the microcontroller 660 via a control signal 714. Uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring respiration; detecting the motion of heart valves; and detecting cardiogenic impedance for use in estimating LAP, etc. Impedance measuring circuit 712 is coupled to switch 674 so that any desired electrode may be used.

In the case where CRMD 100 is intended to operate as an ICD device, it detects the occurrence of an arrhythmia requiring a shock, and automatically applies an appropriate electrical shock therapy to the heart aimed at terminating the arrhythmia. To this end, the microcontroller 660 further controls a shocking circuit 716 by way of a control signal 718. The shocking circuit 716 generates shocking pulses of low (up to 0.5 joules), moderate (0.5-10 joules) or high energy (11 to 40 joules or more), as controlled by the microcontroller 660. Such shocking pulses are applied to the heart of the patient through at least two shocking electrodes, and as shown in this embodiment, selected from the left atrial coil electrode 628, the RV coil electrode 636, and/or the SVC coil electrode 638. The housing 640 may act as an active electrode in combination with the RV electrode 636, or as part of a split electrical vector using the SVC coil electrode 638 or the left atrial coil electrode 628 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 10-40 joules or more), delivered asynchronously (since R-waves may be too disorganized), and pertaining exclusively to the treatment of fibrillation. Accordingly, the microcontroller 660 is capable of controlling synchronous or asynchronous delivery of shocking pulses.

An internal warning device 699 may be provided for generating perceptible warning signals to the patient pertaining to cardiac rhythm irregularities or other issues. The warning signals are generated via vibration, voltage or other methods.

Insofar as PAP is concerned, the microcontroller includes an on-board PAP monitor 701 operative to perform or control the PAP monitoring functions described above. In this example, the PAP monitor includes: a PAP interval detector 703 operative to input PAP signals received from the PAP sensor and detect intervals within the PAP signal corresponding to durations of cardiac cycles. A PAP interval stability detector 705 assesses the stability of the intervals to, for example, detect and distinguish arrhythmias. A PAP interval duration detector 707 assesses interval durations to, for example, detect and distinguish PACs and PVCs. A PAP interval-based cardiac rhythm irregularity detector 709 processes data from detectors 705 and 707 and from other sources to detect cardiac rhythm irregularities based on the intervals within the PAP signal. As explained above, this may be performed to corroborate cardiac rhythm irregularities detected based on IEGMs, to generate additional diagnostic data or for other purposes. As shown, the cardiac rhythm irregularity detector 709 may include a PAC/PVC discrimination system 711 and an AF/VF/VT discrimination system 713. Additionally, if the CRMD is equipped to sense time-varying LAP signals, the CRMD may be provided with an LAP-based cardiac rhythm irregularity detector 715 operative to perform the LAP-based detection techniques described above. A diagnostic controller 717 controls the generation and recordation of diagnostics pertaining to PAP or LAP, irregular cardiac rhythms or other matters. Warnings or alerts may be generated under the control of warning controller 719.

Depending upon the implementation, the various components of the microcontroller may be implemented as separate software modules or the modules may be combined to permit a single module to perform multiple functions. Although shown as components of the microcontroller, some or all of the components may be implemented separately from the microcontroller, using application specific integrated circuits (ASICs) or the like. As already explained, some or all of the techniques described herein can be performed by (or under the control of) an external device such as an external PAP monitor. Within FIG. 12, external system 116 is shown as including a PAP/LAP monitor 723, which may include components corresponding to blocks 701-719.

In general, while the invention has been described with reference to particular embodiments, modifications can be made thereto without departing from the scope of the invention. Note also that the term "including" as used herein is intended to be inclusive, i.e. "including but not limited to."

What is claimed is:

1. A method for use with an implantable pulmonary artery pressure sensor for implant within a patient, the method comprising:
   sensing a pulmonary artery pressure (PAP) signal representative of variations in PAP occurring during cardiac cycles of the patient;
   detecting intervals within the PAP signal corresponding to durations of the cardiac cycles;
   detecting one or more cardiac rhythm irregularities, including premature contractions, based on the intervals within the PAP signal, and
   delivering cardiac therapy to the patient in response to the detection of an irregularity.

2. The method of claim 1 wherein detecting intervals within the PAP signal includes:
   detecting one or more fiducial points within the PAP signal; and
   measuring one or more intervals between the fiducial points corresponding to durations of cardiac cycles.

3. The method of claim 2 wherein the fiducial points include one or more of a pulmonary artery systole (PAS) point, a pulmonary artery diastole (PAD) point and a dicrotic notch.

4. The method of claim 1 wherein detecting a cardiac rhythm irregularity based on the intervals within the PAP signal includes:
   evaluating a stability of the intervals of the PAP signal; and
   detecting the cardiac rhythm irregularity based on the stability of the intervals.

5. The method of claim 4 wherein evaluating the stability of the intervals within the PAP signal includes:
   tracking PAP intervals over a plurality of cardiac cycles;
   rejecting the longest and shortest intervals;
   selecting the second longest and second shortest intervals; and
   determining a difference between the second longest and second shortest intervals as a stability indicator.

6. The method of claim 4 wherein determining the stability of the intervals within the PAP signal includes:
   calculating an average PAP waveform interval stability value; and
   comparing the average PAP waveform interval stability value to a baseline PAP waveform interval stability to generate a stability indicator.

7. The method of claim 4 wherein detecting the cardiac rhythm irregularity based on the stability of the intervals of the PAP signal includes:
   comparing the stability of the intervals of the PAP signal against a stability criteria indicative of irregular cardiac rhythm; and
   generating an indication of irregular cardiac rhythm if the stability is found to be unstable relative to the stability criteria.

8. The method of claim 7 wherein the stability criteria is one or more of a programmed threshold value and a patient baseline threshold value.

9. The method of claim 7 wherein, if an irregular cardiac rhythm is indicated the method further comprises, discriminating the type of irregular cardiac rhythm by:
   detecting a ventricular rate from the intervals;
   comparing the ventricular rate against a tachycardia rate threshold indicative of tachycardia; and
   generating an indication of atrial fibrillation (AF) with controlled ventricular response if the ventricular rate is below the tachycardia rate threshold.

10. The method of claim 9 wherein, if an irregular cardiac rhythm is indicated but the ventricular rate is not below the tachycardia rate threshold the method further comprises:
    detecting a parameter representative of waveform morphology of the PAP signal;
    comparing the parameter representative of the waveform morphology to a baseline morphology parameter associated with normal sinus rhythm to generate a morphology match indicator; and
    detecting a peak within the PAP signal indicative of pulmonary artery systole (PAS) and assessing any significant reduction in PAS from a baseline peak amplitude;
    wherein if the PAS peaks are relatively inconsistent and the morphology match indicator indicates a relatively poor morphology match, an indication of ventricular fibrillation (VF) is generated; and
    if the PAS peaks are relatively consistent and the morphology match indicator indicates a relatively good morphology match, an indication of atrial fibrillation (AF) with rapid ventricular response is generated.

11. The method of claim 4 further including discriminating ventricular tachycardia (VT) from normal sinus rhythm in circumstances where the PAP signal intervals are relatively stable.

12. The method of claim 11 wherein discriminating VT from normal sinus rhythm in circumstances where the PAP signal intervals are relatively stable includes:
    detecting a ventricular rate from the intervals;

comparing the ventricular rate against a tachycardia rate threshold indicative of tachycardia; and generating an indication of VT if the rate exceeds the threshold and generating an indication of normal sinus rhythm otherwise.

13. The method of claim 1 wherein detecting premature contractions includes:

determining a duration of an interval within the PAP signal corresponding to an individual cardiac cycle;

comparing the duration against a premature contraction threshold; and generating an indication of a premature contraction if the duration is below the premature contraction threshold.

14. The method of claim 13 further including discriminating premature atrial contractions (PACs) and premature ventricular contractions (PVCs) by:

detecting a parameter representative of waveform morphology of the PAP signal;

comparing the parameter representative of the waveform morphology to a baseline morphology parameter associated with normal sinus rhythm to generate a morphology match indicator; and detecting a peak within the PAP signal indicative of pulmonary artery systole (PAS) and assessing any significant reduction in PAS peak amplitude from a baseline peak amplitude;

wherein if the PAS peaks are relatively inconsistent and the morphology match indicator indicates a relatively poor morphology match, the premature contraction is identified as a PVC; and if the PAS peaks are relatively consistent and the morphology match indicator indicates a relatively good morphology match, the premature contraction is identified as a PAC.

15. The method of claim 14 further including, in response to detection of a PVC, recording diagnostics representative of one or more of: the PAP signal, the PAS peak, the ventricular rate and any trends therein.

16. The method of claim 1 further including discriminating premature atrial contractions (PACs) and premature ventricular contractions (PVCs) by:

calculating a correlation coefficient associated with the PAP signal and signals representative of known PACs and known PVCs; and discriminating PACs and PVCs based on the correlation coefficient.

17. The method of claim 16 wherein calculating the correlation coefficient associated with the PAP signal uses a kendall tau coefficient.

18. The method of claim 1 further including:

sensing a left atrial pressure (LAP) signal representative of variations in LAP during individual heart beats; and detecting a cardiac rhythm irregularity based, in part, on the LAP signal.

19. The method of claim 18 further wherein detecting a cardiac rhythm irregularity based, in part , on the LAP signal includes one or more of:

morphology matching; frequency spectrum analysis to distinguish atrial rhythms from ventricular rhythms; and frequency spectrum analysis to evaluate a dominate frequency to discriminate high rate arrhythmias based on frequency.

20. The method of claim 1 wherein at least some of the steps are performed by an external system that receives PAP signals from the implantable PAP sensor.

21. The method of claim 1 wherein at least some of the steps are performed by an implantable cardiac rhythm management device that receives PAP signals from the implantable PAP sensor.

22. A system for use with an implantable pulmonary artery pressure sensor for implant within a patient, the system comprising:

a pulmonary artery pressure (PAP) signal input system operative to receive PAP signals from the PAP sensor wherein the PAP signal is representative of variations in PAP occurring during cardiac cycles of the patient;

a PAP interval detector operative to detect intervals within the PAP signal corresponding to durations of the cardiac cycles;

a PAP interval-based cardiac rhythm irregularity detector operative to detect a cardiac rhythm irregularity including premature contractions, based on the intervals within the PAP signal; and a pulse generator coupled to the PAP interval-based cardiac rhythm irregularity detector, the pulse generator being adapted to deliver cardiac therapy to the patient in response to the detection of a rhythm irregularity.

23. The system of claim 22 wherein the system includes an implantable cardiac rhythm management device equipped to provide electrical cardiac stimulation to the heart of a patient when the device is implanted.

24. The system of claim 22 wherein the system includes an external PAP monitor operative to receive PAP signals from the implantable PAP sensor.

25. A system for use with an implantable pulmonary artery pressure sensor for implant within a patient, the system comprising:

means for sensing a pulmonary artery pressure (PAP) signal representative of variations in PAP occurring during cardiac cycles of the patient;

means for detecting intervals within the PAP signal corresponding to durations of the cardiac cycles;

means for detecting a cardiac rhythm irregularity, including premature contractions, based on the intervals within the PAP signal; and means for delivering cardiac therapy to the patient in response to the detection of a cardiac rhythm irregularity.

* * * * *